(12) United States Patent  (10) Patent No.: US 7,655,684 B2
Schilling et al.  (45) Date of Patent: *Feb. 2, 2010

(54) INHIBITORS OF GLUTAMINYL CYCLASE

(75) Inventors: Stephan Schilling, Halle/Saale (DE);
Andre Johannes Niestroj, Sennewitz (DE); Ulrich Heiser, Halle/Saale (DE);
Hans-Ulrich Demuth, Halle/Saale (DE);
Mirko Buchholz, Sennewitz (DE)

(73) Assignee: Probiodrug AG, Halle-Saale (DE)

( * ) Notice: Subject to any disclaimer, the term of this patent is extended or adjusted under 35 U.S.C. 154(b) by 6 days.

This patent is subject to a terminal disclaimer.

(21) Appl. No.: 12/046,520

(22) Filed: Mar. 12, 2008

(65) Prior Publication Data

US 2008/0153892 A1 Jun. 26, 2008

Related U.S. Application Data

(62) Division of application No. 10/838,993, filed on May 5, 2004, now Pat. No. 7,371,871.

(60) Provisional application No. 60/468,014, filed on May 5, 2003.

(51) Int. Cl.
*A61K 31/4174* (2006.01)
(52) U.S. Cl. ...................................... 514/396
(58) Field of Classification Search .................. 514/396
See application file for complete search history.

(56) References Cited

U.S. PATENT DOCUMENTS 5,552,426 A 9/1996 Lunn et al.
6,448,282 B1 9/2002 Phillips et al.

FOREIGN PATENT DOCUMENTS

| WO | 93/001812 | 2/1993 |
|----|-----------|--------|
| WO | 93/020061 | 10/1993 |
| WO | 95/022327 | 8/1995 |
| WO | 99/041220 | 8/1999 |
| WO | 99/041224 | 8/1999 |
| WO | 00/05053596 A2 | 9/2000 |
| WO | 00/05053596 A3 | 9/2000 |
| WO | 02/013821 | 2/2002 |
| WO | 03/0070732 | 8/2003 |
| WO | 04/089366 | 10/2004 |
| WO | 04/098591 | 11/2004 |

OTHER PUBLICATIONS

Clader, John W. et al., Substituted (1,2-Diarylethyl)amide Acyl-CoA:Cholesterol Acyltransferase Inhibitors: Effect of Polar Groups on in Vitro and in Vivo Activity, J. Med Chem 1995, 38, 1600-1607.

(Continued)

*Primary Examiner*—Laura L. Stockton
(74) *Attorney, Agent, or Firm*—Sonnenschein Nath & Rosenthal LLP

(57) ABSTRACT

Compounds that act as inhibitors of QC including those represented by the general formulae 1 to 9:

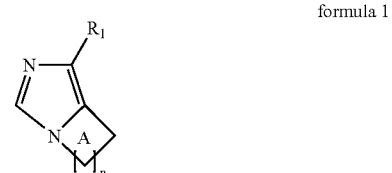

formula 1

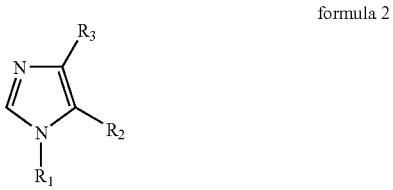

formula 2

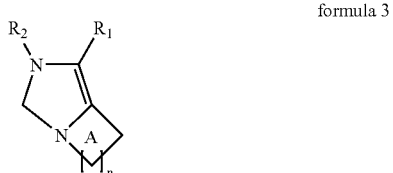

formula 3

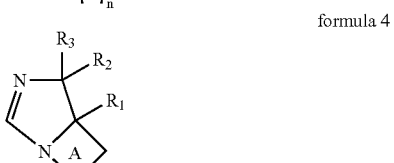

formula 4

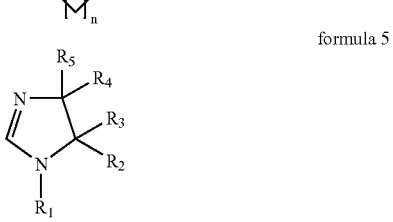

formula 5

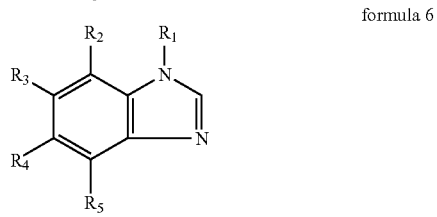

formula 6 and combinations thereof for the treatment of neuronal disorders, especially Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

18 Claims, No Drawings

OTHER PUBLICATIONS

Ganelin, C. Robin et al, Design of potent non-thiourea H3-Receptor histamine antagonists, J. Med Chem. 1995, 38 3342-3350.

Liu, Shenquan et al., Nonpeptide somatostatin agonists with sst4 selectivity: synthesis and structure-activity relationships of thioureas J. Med Chem. 1998, 41, 4693-4705.

Misquitta, Stephanie A. et al., Inhibitions Studies of Glutaminyl Cyclase, FASEB Journal 2001.

Misquitta, Stephanie A. et al., Characterization of the inhibition of glutaminyl cyclase by imidozole derivatives and phenathorolines, FASEB Annual meeting, 2002.

Moon, Malcolm et al. Cholinergic activity and acetylenic imidazoles and related compounds J. Med. Chem 1991, 34, 2314-2327.

Schilling, Stephan et al., Glutaminyl cyclases unfold glutamyl cyclase activity under mild acid conditions, FEBS Letters 563, 2004, 191-196.

Venkatachalam, T.K. et al., Anti-HIV activity of aromatic and heterocylic thiazolyl thiourea compounds, Bioorganic & Medicinal Chemistry Letters 2001, 11, 523-528.

Wright, William B. et al., Thromboxane synthetase inhibitors and antihypertensive agents. J. Med. Chem 1986, 29, 523-530.

Wright, William B. et al., Thromboxane synthetase inhibitors and antihypertensive agents. J. Med. Chem 1987, 30, 2277-2283.

INHIBITORS OF GLUTAMINYL CYCLASE

CROSS-REFERENCE TO RELATED APPLICATIONS

The present application is a Divisional application of U.S. application Ser. No. 10/838,993, filed on May 5, 2004, which claims priority to U.S. Provisional Application Ser. No. 60/468,014, filed on May 5, 2003. Each of the above applications are incorporated herein by reference in their entirety to the extent permitted by law.

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 *Nature* 4874, 1299). 24 years later, a corresponding enzymatic activity was discovered in animal pituitary (Busby, W. H. J. et al. 1987 *J Biol Chem* 262, 8532-8536; Fischer, W. H. and Spiess, J. 1987 *Proc Natl Acad Set USA* 84, 3628-3632). For the mammalian QC, the conversion of Gln into pGlu by QC could be shown for the precursors of TRH and GnRH (Busby, W. H. J. et al. 1987 *J Biol Chem* 262, 8532-8536; Fischer, W. H. and Spiess, J. 1987 *Proc Natl Acad Sci USA* 84, 3628-3632). In addition, initial localization experiments of QC revealed a co-localization with its putative products of catalysis in bovine pituitary, further improving the suggested function in peptide hormone synthesis (Bockers, T. M. et al. 1995 *J Neuroendocrinal* 7, 445-453). In contrast, the physiological function of the plant QC is less clear. In case of the enzyme from *C. papaya*, a role in the plant defense against pathogenic microorganisms was suggested (El Moussaout, A. et al. 2001 *Cell Mol Life Sci* 58, 556-570). Putative QCs from other plants were identified by sequence comparisons recently (Dahl, S. W. et al. 2000 *Protein Expr Purif* 20, 27-36) The physiological function of these enzymes, however, is still ambiguous. The QCs known from plants and animals show a strict specificity for L-Glutamine in the N-terminal position of the substrates and their kinetic behavior was found to obey the Michaelis-Menten equation (Pohl, T. et al. 1991 *Proc Natl Acad Sci USA* 88, 10059-10063; Consalvo, A. P. et al. 1988 *Anal Biochem* 175, 131-138; Gololobov, M. Y. et al. 1996 *Biol Chem Hoppe Seyler* 377, 395-398). A comparison of the primary structures of the QCs from *C. papaya* and that of the highly conserved QC from mammals, however, did not reveal any sequence homology (Dahl, S. W. et al. 2000 *Protein Expr Purif* 20, 27-36). Whereas the plant QCs appear to belong to a new enzyme family (Dahl, S. W. et al. 2000 *Protein Expr Purif* 20, 27-36), the mammalian QCs were found to have a pronounced sequence homology to bacterial aminopeptidases (Bateman, R. C. et al. 2001 *Biochemistry* 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed Glu1-conversion is favored around pH 6.0 while Gln1-conversion to pGlu-derivatives occurs with a pH-optimum of around 8.0. Since the formation of pGlu-A□-related peptides can be suppressed by inhibition of recombinant human QC and QC-activity from pig pituitary extracts, the enzyme QC is a target in drug development for treatment of Alzheimer's disease.

EP 02 011 349.4 discloses polynucleotides encoding insect glutaminyl cyclase, as well as polypeptides encoded thereby. This application further provides host cells comprising expression vectors comprising polynucleotides of the invention, isolated polypeptides and host cells comprising insect QC are useful in methods of screening for agents that reduce glutaminyl cyclase activity. Such agents are useful as pesticides.

Definitions

The term "DP IV-inhibitor" or "dipeptidyl peptidase IV inhibitor" is generally known to a person skilled in the art and means enzyme inhibitors, which inhibit the catalytical activity of DP IV or DP IV-like enzymes.

"DP IV-activity" is defined as the catalytical activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence The term "PEP-inhibitor" or "prolyl endopeptidase inhibitor" is generally known to a person skilled in the art and means enzyme inhibitors, which inhibit the catalytical activity of prolyl endopeptidase (PEP).

The term "QC" as used herein comprises glutaminyl cyclase (QC) and QC-like enzymes. QC and QC-like enzymes have identical or similar enzymatic activity, further defined as QC activity. In this regard, QC-like enzymes; can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

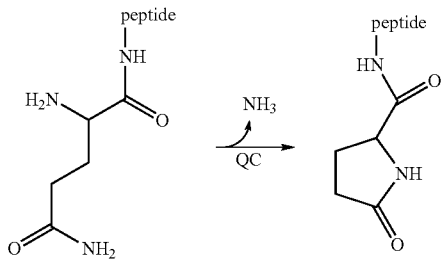

Scheme 2: Cyclization of L-homoglutamine by QC

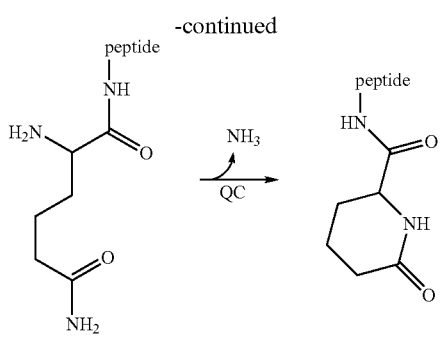

The term "EC" as used herein comprises the side activity of QC and QC-like enzymes as glutamate cyclase (EC), further defined as EC activity.

The expression "QC/EC" refers to the glutaminyl cyclase, which has at least one of QC or EC activity, preferably both, QC and EC activity.

The term "EC activity" as used herein is defined as intramolecular cyclization of N-terminal glutamate residues into pyroglutamic acid (pGlu*) by QC. See therefore scheme 3.

Scheme 3: N-terminal cyclization of uncharged glutamyl peptides by QC (EC)

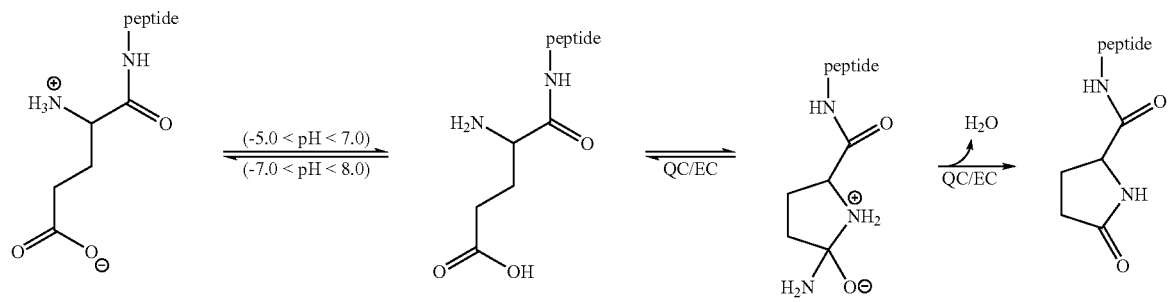

The term "QC-inhibitor" "glutaminyl cyclase inhibitor" is generally known to a person skilled in the art and means enzyme inhibitors, which inhibit the catalytical activity of glutaminyl cyclase (QC) and/or its glutamyl cyclase (EC) activity.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use for example the term "pharmaceutically acceptable" embraces a vetermarily acceptable compound or a compound acceptable in human medicine a health care.

Throughout the description and the claims the expression "acyl" can denote a $C_{1-20}$ acyl residue, preferably a $C_{1-8}$ acyl residue and especially preferred a $C_{1-4}$ acyl residue; "cycloalkyl" can denote a $C_{3-12}$ cycloalkyl residue, preferably a $C_4$, $C_5$ or $C_6$ cycloalkyl residue; and "a carbocycle" can denote a $C_{3-12}$ a carbocycle residue, preferably a $C_4$, $C_5$ or $C_6$ a carbocycle residue. "Heteroaryl" is defined as an aryl residue, wherein 1 to 4, and more preferably 1, 2 or 3 ring atoms are replaced by heteroatoms like N, S or O. "A heterocycle" is defined as a cycloalkyl residue, wherein 1, 2 or 3 ring atoms are replaced by heteroatoms like N, S or O. "Peptides" are selected from dipeptides to decapeptides, preferred are dipeptides, tripeptides, tetrapeptides and pentapeptides. The amino acids for the formation of the "peptides" can be selected from those listed above.

Throughout the description and the claims the expression "alkyl" can denote a $C_{1-50}$ alkyl group, preferably a $C_{6-30}$ alkyl group, especially a $C_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms, the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-}$ alkynyl group, preferably a $C_{2-6}$ alkynyl group, which has the triple bond(s) at any desired location and may be substituted or unsubstituted.

The expression "substituted" or substituent can denote any desired substitution by one or more, preferably one or two, alkyl, alkenyl, alkynyl, mono- or multi-valent acyl, alkanoyl, alkoxyalkanoyl or alkoxy alkyl groups; the afore-mentioned substituents may in turn have one or more (but preferably zero) alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae $(alkyl)_2N$— or alkyl-NH—, —CO—$N(alkyl)_2$ or —CO—NH(alkyl), -alkyl-OH or -alkyl-COOH. Furthermore, the expression "substituted" or "substituent" can denote one or two of each, branched or unbranched alkyl chain, a branched or unbranched alkenyl chain, a branched or unbranched alkynyl chain, a carbocycle, aryl, heteroaryl, a heterocycle; the afore-mentioned substituents may in turn have one or more branched or unbranched alkyl chain, a branched or unbranched alkenyl chain, a branched or unbranched alkynyl chain, a carbocycle, aryl, heteroaryl, a heterocycle as side group(s); all herein before mentioned chains, residues or side groups may contain one or more, preferably one or two, epoxy moiety(ies) and one or more, preferably one or two, substituted or unsubstituted aziridine(s), whereas the substitution is characterized again as $R_1$ which is described above; all chains, residues or side groups may be substituted by one or more F, Cl, Br, I, $NH_2$, NO, $NO_2$, CN atoms or groups, isocyanide(s), cyanate(s), isocyanate(s), fulminate(s), thiocyanate(s), isothiocyanate(s), selenocyanate(s) and isoselenocyanate(s), thio acids of sulphur with empirical formulae —$S_2H$, —$S_2OH$, —$S_3H$, —$S_2O_2H$, —$S_3OH$, and —$S_4H$ and their derivatives, whereas the substitution is characterized as $R_1$; azonic acid(s), azinic acid(s), sulphonic acid(s) ($SO_2H$), sulphur acid(s) ($SO_3H$) and their esters, whereas the ester residue(s) is characterized as $R_1$; phosphinous acid(s), phosphonous acid(s), phosphinic acid(s), phosphonic acid(s), their replaced modifications like phosphinothioic O-acid(s), phosphinothioic S-acid(s), phosphinimidic acid(s), phosphonothioic O,O'-acid(s), phosphonothioc O,S-acid(s), phosphonimidothioic acid(s) and their esters, whereas the ester residue(s) is characterized as $R_1$.

Furthermore, all afore-mentioned chains, residues or side groups may contain one or more, preferably one, two or three alcohol(s), acid(s), aldehyde(s) or ketone(s), phosphane(s), phosphorane(s), sulfoxides (SO), sulfones ($SO_2$), their selenium or tellurium analogues named selenoxide and selenone, sulfonic anhydride(s) $[(SO_2)_2O]$ and sulphonic anhydride(s) $[(SO)_2O]$, hydrazide(s), N-Oxides of azo compounds; as well as amine(s), amide(s), ester(s), ether(s) or sulfonamid(e), phosphane(s) or phosphorane(s), having the formulae —$NHR_1$ or —$N(R_1)_2$, —$CON(R_1)_2$ or —$CONHR_1$, —CO—$OR_1$, $R_1$—O—$R_1$, —$SO_2N(R_1)_2$ or —$SO_2NHR_1$, —$PHR_1$, —$P(R_1)2$, —$PH_3R_1$, —$PH_2(R_1)_2$, —$PH(R_1)_3$, —$P(R_1)_4$, whereas $R_1$ is described above; as well as the corresponding thio analogues of the in advance described residues, where the oxygen is replaced by sulphur, for example thiol(s), thioaldehyde(s) and thioketone(s).

Amino acids which can be used in the present invention are L and D-amino acids, N-methyl-amino acids, aza-amino acids; allo- and threo-forms of Ile and Thr, which can, e.g. be α-, β- or ω-amino acids, whereof α-amino acids are preferred.

Examples of amino acids are:

aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly). N-methylisoleucine (N-MeIle), phenylglycine (Phg), cyclohexyl alanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethyl-cysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic acids. Examples of ω-amino acids are e.g.: 5-Ara (aminoraleric acid), 6-Ahx (aminohexanoic acid), 8-Aoc (aminooctanoic acid), 9-Anc (aminovanoic aicd), 10-Adc (aminodecanoie acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal) and (2-Nal), 4-aminophenylalanine (Phe(4-$NH_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe(3,4-$C_{12}$)), 3-fluorophenylalanine (Phe(3-F)), 4-fluorophenylalanine (Phe(4-F)), 3,4-fluorophenylalanine (Phe(3,4-$F_2$)), pentafluorophenylalanine (Phe($F_5$)), 4-guanidinophenylalanine (Phe(4-guanidino)), homophenylalanine (hPhe), 3-jodophenylalanine (Phe(3-J)), 4-jodophenylaline (Phe(4-J)), 4-methylphenylalanine (Phe(4-Me)), 4-nitrophenylalanine (Phe-4-$NO_2$)), biphenylalanine (Bip), 4-phosphonomethylphenylalanine (Pmp), cyclohexylglycine (Ghg), 3-pyridinylalanine (3-Pal). 4-pyridmylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-$J_2$)), methyltyrosine (Tyr(Me)), 2',6'-dimethyltyrosine (Dmt), 3-$NO_2$-tyrosine (Tyr(3-$NO_2$)), phosphotyrosine (TyrP$O_3H_2$)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Ate), diaminoacetic acid (Gly($NH_2$)), diaminobutyric acid (Dab), 1,3-dihydro-2H-isoinole-carboxylic acid (Disc), homocylcohexylalanine (hCha), homophenylalanine (hPhe or Hof), trans-3-phenyl-azetidine-2-carboxylic acid, 4-phenylpyrrolidine-2-carboxylic acid, 5-phenyl-pyrrolidine-2-carboxylic acid, 3-pyridylalanine (3-Pya), 4-pyridylalamine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha).

"Peptides" are selected from dipeptides to decapeptides, preferred are dipeptides, tripeptides, tetrapeptides and pentapeptides. The amino acids for the formation of the "peptides" can be selected from those listed above.

An "aza-amino acid" is defined as an amino acid where the chiral α-CH group is replaced by a nitrogen atom, whereas an "aza-peptide" is defined as a peptide, in which the chiral □-CH group of one or more amino acid residues in the peptide chain is replaced by a nitrogen atom.

Other amino acid substitutions for those encoded in the genetic code can also be included in peptide compounds within the scope of the invention and can be classified within this general scheme. Proteinogenic amino acids are defined as natural protein-derived α-amino acids. Non-proteinogenic amino acids are defined as all other amino acids, which are not building blocks of common natural proteins.

"Peptide mimetics" per se are known to a person skilled in the art. They are preferably defined as compounds which have a secondary structure like a peptide and optionally further structural characteristics; their mode of action is largely similar or identical to the mode of action of the native peptide; however, their activity (e.g. as an antagonist or inhibitor) can he modified as compared with the native peptide, especially visa vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999.

The aim for using these mimetic structures is increasing the activity, increasing the selectivity to decrease side effects, protect the compound against enzymatic degradation for prolongation of the effect.

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and isolation of stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Pharmaceutically acceptable salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

Polymorph crystal forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed H. Bundgaard, Elsevier, 1985 and the patent applications DE 198 28 113, DE 198 28 114, WO 99/67228 and WO 99/67279 which are folly incorporated herein by reference.

Protective groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and additives for galenic formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives Include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, poly hydroxy butyeric acid, polyorthoesters, polyacetals, polydihydropyrans, polycyanoaerylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Peptide Sequences

The peptides mentioned and used herein have the following sequences:

Aβ(1-42):
Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala(SEQ ID NO: 1)

Aβ(1-40):
Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val(SEQ ID NO: 2)

Aβ(3-42):
Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala(SEQ ID NO: 3)

Aβ(3-40):
Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val(SEQ ID NO: 4)

Aβ(1-11)a:
Asp-Ala-Glu-Phe-Arg-His-Asp-Ser-Gly-Tyr-Glu-NH$_2$
(SEQ ID NO: 5)

Aβ(3-11)a:
Glu-Phe-Arg-His-Asp-Ser-Gly-Tyr-Glu-NH$_2$
(SEQ ID NO: 6)

Aβ(1-21)a:
Asp-Ala-Glu-Phe-Arg-His-Asp-Ser-Gly-Tyr-Glu-Val-His-His-Gln-Lys-Leu-Val-Phe-Phe-Ala-NH$_2$
(SEQ ID NO: 7)

Aβ(3-21)a:
Glu-Phe-Arg-His-Asp-Ser-Gly-Tyr-Glu-Val-His-His-Gln-Lys-Leu-Val-Phe-Phe-Ala-NH$_2$
(SEQ ID NO: 8)

Gln$^3$-Aβ(3-40):
Gln-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu Met-Val-Gly-Gly-Val-Val(SEQ ID NO: 9)

Gln$^3$Aβ(3-21)a:
Gln-Phe-Arg-His-Asp-Ser-Gly-Tyr-Glu-Val-His-His-Gln-Lys-Leu-Val-Phe-Phe-Ala-NH$_2$
(SEQ ID NO: 10)

Gln$^3$-Aβ(1-11)a:
Asp-Ala-Gln-Phe-Arg-His-Asp-Ser-Gly-Tyr-Glu-NH$_2$
(SEQ ID NO: 11)

Gln$^3$-Aβ(3-11)a:
Gln-Phe-Arg-His-Asp-Ser-Gly-Tyr-Glu-NH$_2$
(SEQ ID NO: 12)

SUMMARY OF THE INVENTION

The present invention provides compounds that act as inhibitors of glutaminyl cyclase (QC, EC 2.3.2.5). Those compounds are represented by the general formulae 1 to 6.

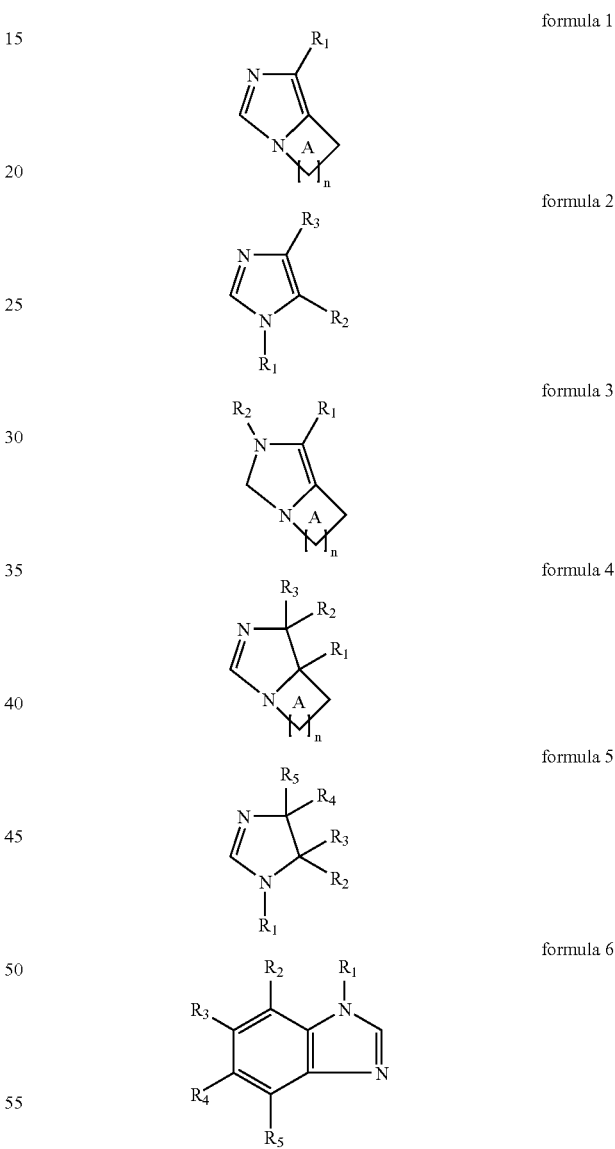

Physiological substrates of QC in mammals are, e.g. [Glu$^3$] amyloid [β-protein (3-40/42), [Gln$^3$] amyloid (β-protein (3-40/42), Gastrin, Neurotensin, FPP, CCL 2, CCL 7, CCL 8, CCL 16, CCL 18, Fractalkine, Orexin A, [Gln$^3$]-glueagon(3-29) and [Gln$^5$]-substance P(5-11). The compounds according to the present invention and pharmaceutical compositions comprising at least one compound according to the present invention are useful for the treatment of conditions that can be treated by modulation of QC activity.

By administering inhibitors of QC/EC activity to a mammal it can be possible to prevent or alleviate or treat neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC/EC activity in combination with other agents, especially for the treatment of neuronal disorders.

DETAILED DESCRIPTION OF THE INVENTION

The present invention provides compounds having the general formula 1 and the pharmaceutically acceptable salts thereof, including all stereoisomers:

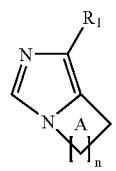

formula 1 wherein n is 1, 2, 3 or 4, preferably 2 or 3, especially 2, and A can be a saturated or unsaturated heterocycle and may be substituted or unsubstituted, and wherein $R_1$ is H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$ optionally being substituted independently of each other.

In addition, the present invention relates to compounds which can be described generally by the the general formula 2 and the pharmaceutically acceptable salts thereof, including all stereoisomers;

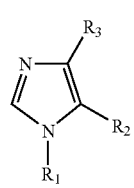

formula 2 wherein $R_1$, $R_2$ and $R_3$ are independently 11 or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$ and $R_3$ optionally being substituted independently of each other.

Furthermore, the present invention relates to compounds which can be described generally by the general formula 3 and the pharmaceutically acceptable salts thereof including all stereoisomers:

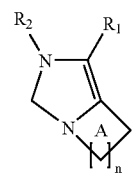

formula 3 wherein n is 1, 2, 3 or 4, preferably 2 or 3, especially 2, and A can be a saturated or unsaturated heterocycle and may be substituted or unsubstituted, and wherein $R_1$ and $R_2$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$ and $R_2$ optionally being substituted independently of each other.

Furthermore, the present invention relates to compounds which can be described generally by the general formula 4 and the pharmaceutically acceptable salts thereof including all stereoisomers:

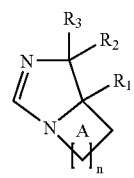

formula 4 wherein n is 1, 2, 3 or 4, preferably 2 or 3, especially 2, and A can be a saturated or unsaturated heterocycle and may be substituted or unsubstituted, and wherein $R_1$, $R_2$ and $R_3$ are independently H or a branched or unbranched alkyl chain, a branched or unbranched alkenyl chain, a branched or unbranched alkynyl chain, a carbocycle, aryl, heteroaryl, a heterocycle, azaamino acid, amino acid or a mimetic thereof, aza-peptide, peptide or a mimetic thereof; all of the above residues $R_1$, $R_2$ and $R_3$ optionally being substituted independently of each other.

Furthermore, the present invention relates to compounds which can be described generally by the general formula 5 and the pharmaceutically acceptable salts thereof, including all stereoisomers:

formula 5

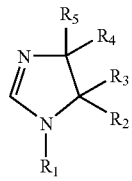

wherein $R_1$, $R_2$, $R_3$, $R_4$ and $R_5$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$, $R_3$, $R_4$ and $R_5$ optionally being substituted independently of each other.

Furthermore, the present invention relates to compounds which can be described generally by the general formula 6 or the pharmaceutically acceptable salts thereof including all stereoisomers:

formula 6

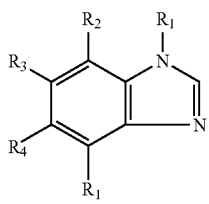

wherein $R_1$, $R_2$, $R_3$, $R_4$ and $R_5$ are independently H or a branched or unbranched alkyl chain, a branched or unbranched alkenyl chain, a branched or unbranched alkynyl chain, a carbocycle, aryl, heteroaryl, a heterocycle, aza-amino acid, amino acid or a mimetic thereof, aza-peptide, peptide or a mimetic thereof; all of the above residues $R_1$, $R_2$, $R_3$, $R_4$ and $R_5$ optionally being substituted independently of each other.

Preferred structures relate to formula 2a:

formula 2a

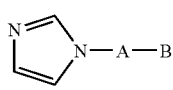

wherein A is a branched or unbranched $C_1$-$C_7$ alkyl chain, a branched or unbranched $C_1$-$C_7$ alkenyl chain, a branched or unbranched $C_1$-$C_7$ alkynyl chain, or wherein A is a compound selected from the group consisting of.

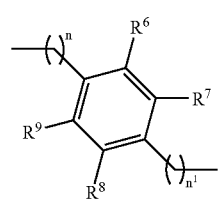 (I)

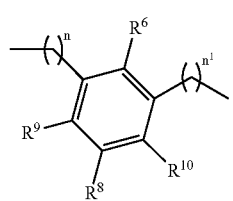 (II)

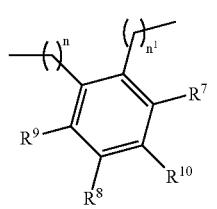 (III)

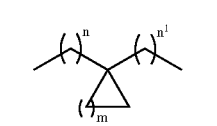 (IV)

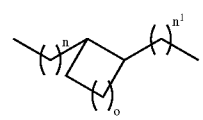 (V)

wherein $R^6$-$R^{10}$ are independently H or a branched or unbranched alkyl chain, a branched or unbranched alkenyl chain, a branched or unbranched alkynyl chain, a carbocycle, aryl, heteroaryl, a heterocycle, preferably H or methyl, wherein n and $n^1$ are independently 1-5, m is 1-5, o is 0-4, Preferably A is a $C_3$ alkyl chain, a $C_3$ methyl branched alkyl chain, cycloalkyl-1,1-dimethyl of formula (IV) with m=1-4, 1,4-dimethylphenyl or 1,3-dimethyl phenyl; and wherein B is a compound selected from the group consisting of

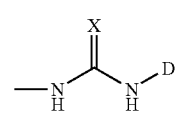 (VI)

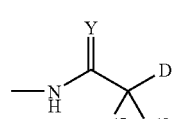 (VII)

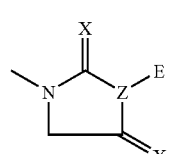 (VIII)

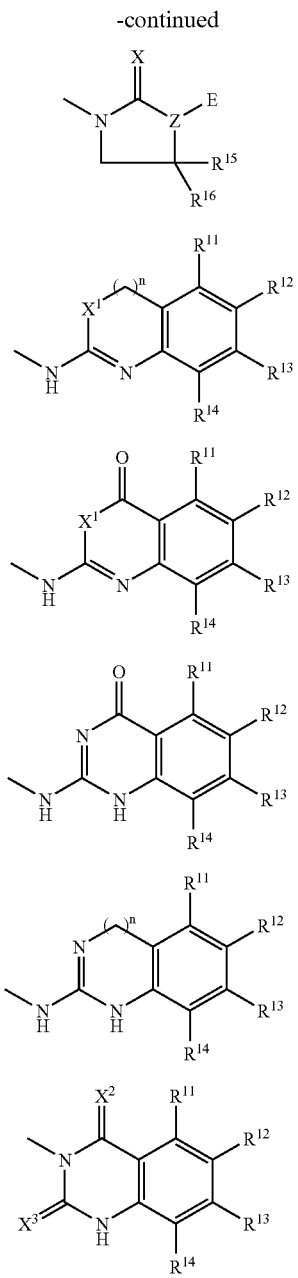

wherein D and E are a branched or unbranched alkyl chain, a branched or unbranched alkenyl chain, a branched or unbranched alkynyl chain, a carbocycle, aryl, heteroaryl, a heterocycle.

Preferably D and E are a substituted phenyl, wherein substitution means oxyalkyl, thioalkyl, halogenyl, or carboxylic acid alkyl ester or aryl ester.

Further preferred are compounds, wherein D and E are a dihydrobenzodioxine, a benzodioxole, a benzodithiole, a dihydrobenzodithiine, a benzooxathiole, a dihydrobenzooxathiine.

wherein Z is CH or N.

In a preferred embodiment Z is N.

wherein X can be O, S, N—CN, with the proviso for formulas (VIII) and (IX) that, if Z=CH, X is O or S.

wherein $X^1$, $X^2$ and $X^3$ are independently O or S,

In a preferred embodiment, X is S.

wherein Y is O or S, wherein $R^{11}$-$R^{14}$ are independently H or a branched or unbranched alkyl chain, a branched or unbranched alkenyl chain, a branched or unbranched alkynyl chain, a carbocycle, aryl, heteroaryl, a heterocycle, halogenyl, oxyalkyl, thioalkyl, carboxyl, carboxylic acid ester, carbonyl, carbamide, carbimide, thiocarbamide orthiocarbonyl.

In a preferred embodiment, $R^{11}$ and $R^{14}$ are H.

In a further preferred embodiment, $R^{12}$ and $R^{13}$ are independently oxyalkyl or thioalkyl, halogenyl, or carboxylic acid alkyl ester or phenyl, or $R^{12}$ and $R^{13}$ are connected to form a dihydrobenzodioxine, a benzodioxole, a benzodithiole, a dihydrobenzodithiine, a benzooxathiole, a dihydrobenzooxathiine, wherein $R^{15}$ and $R^{16}$ are independently H or a branched or unbranched alkyl chain, or a branched or unbranched alkenyl chain.

In a preferred embodiment, at least one of $R^{15}$ and $R^{16}$ is H.

Most preferably, $R^{15}$ and $R^{16}$ are both H.

wherein $R_{17}$ and $R_{18}$ are independently of each other H or a branched or unbranched alkyl chain, a branched or unbranched alkenyl chain, a branched or unbranched alkynyl chain, a carbocycle, aryl or can be connected to form a carbocycle with up to 6 ring atoms.

In a preferred embodiment, one of $R^{17}$ and $R^{18}$ is H and the other is Me.

Further preferred are compounds wherein one of $R^{17}$ and $R^{18}$ is H and the other is phenyl.

In a further preferred embodiment, $R^{17}$ and $R^{18}$ may form a carbocycle with up to 6 ring atoms.

wherein n is 0 or 1, all of the above residues being optionally substituted independently of each other.

Furthermore, the present invention provides the use of compounds of the formula 2a

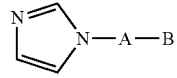

formula 2a for the preparation of a medicament for the treatment of diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia, wherein A is a branched or unbranched $C_1$-$C_7$ alkyl chain, a branched or unbranched $C_1$-$C_7$ alkenyl chain, a branched or unbranched $C_1$-$C_7$ alkynyl chain, or wherein A is a compound selected from the group consisting of:

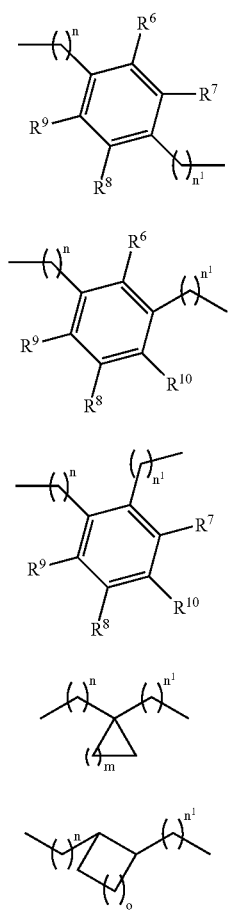

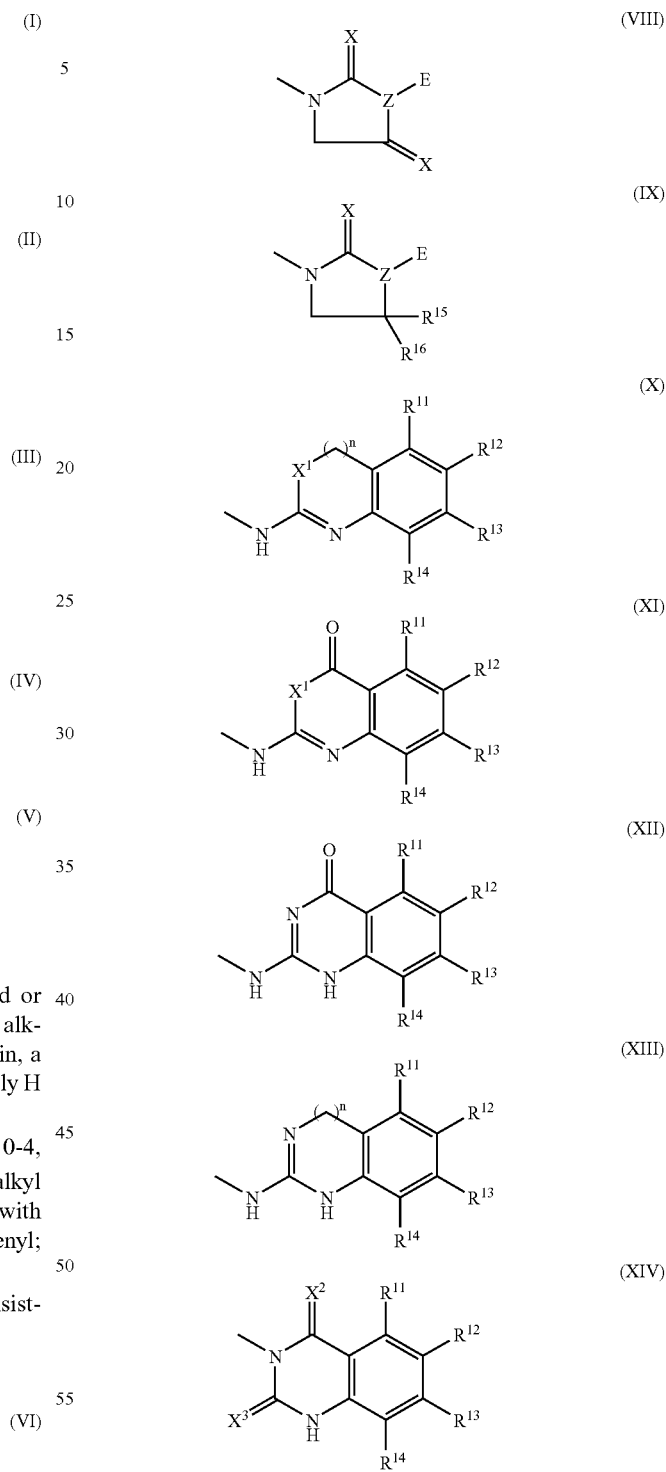

wherein R⁶-R¹⁰ are independently H or a branched or unbranched alkyl chain, a branched or unbranched alkenyl chain, a branched or unbranched alkynyl chain, a carbocycle, aryl, heteroaryl, a heterocycle, preferably H or methyl, wherein n and n¹ are independently 1-5, m is 1-5, o is 0-4, Preferably A is a $C_3$ alkyl chain, a $C_3$ methyl branched alkyl chain, cycloalkyl-1,1-dimethyl of formula (IV) with m=1-4, 1,4-dimethyl phenyl or 1,3-dimethyl phenyl; and wherein B is a compound selected from the group consisting of

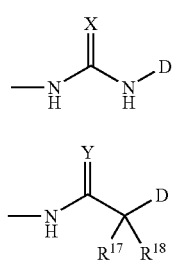

wherein D and E are a branched or unbranched alkyl chain, a branched or unbranched alkenyl chain, a branched or unbranched alkynyl chain, a carbocycle, aryl, heteroaryl, a heterocycle.

Preferably D and E are a substituted phenyl, wherein substitution means oxyalkyl, thioalkyl, halogenyl, carboxylic acid alkyl ester or aryl ester.

Further preferred are compounds, wherein D and E are a dihydrobenzodioxine, a benzodioxole, a benzodithiole, a dihydrobenzodithiine a benzooxathiole, a dihydrobenzooxathiine.

wherein Z is CH or N.

In a preferred embodiment, Z is N.

wherein X can be O, S, N—CN, with the proviso for formulas (VIII) and (IX) that, if Z=CH, X is O or S, wherein $X^1$, $x^2$ and $X^3$ are independently O or S with the proviso for compound (XIV) that at least one of $X^2$ and $X^3$ must be S, In a preferred embodiment, X is S.

wherein Y is O or S, with the proviso that Y may not be 0 when the carbocycle formed by $R^{17}$ and $R^{18}$ has 3 members in the ring.

wherein $R^{11}$-$R^{14}$ are independently H or a branched or unbranched alkyl chain, a branched or unbranched alkenyl chain, a branched or unbranched alkynyl chain, a carbocycle, aryl, heteroaryl, a heterocycle, halogenyl, oxyalkyl, thioalkyl, carboxyl, carboxylic acid ester, carbonyl, carbamide, carbimide, thiocarbamide or thiocarbonyl.

In a preferred embodiment, $R^{11}$ and $R^{14}$ are H.

In a further preferred embodiment, $R^{12}$ and $R^{13}$ are independently oxyalkyl or thioalkyl, halogenyl, or carboxylic acid alkyl ester or phenyl, or $R^{12}$ and $R^{13}$ are connected to form a dihydrobenzodioxine, a benzodioxole, a benzodithiole, a dihydrobenzodithiine, a benzooxathiole, a dihydrobenzooxathiine, wherein $R^{15}$ and $R^{16}$ are independently H or a branched or unbranched alkyl chain, or a branched or unbranched alkenyl chain.

In a preferred embodiment, one of $R^{15}$ and $R^{16}$ is H.

Most preferably, $R^{15}$ and $R^{16}$ are both H.

wherein $R^{17}$ and $R^{18}$ are independently H or a branched or unbranched alkyl chain, a branched or unbranched alkenyl chain, a branched or unbranched alkynyl chain, a carbocycle, aryl or can be connected to form a carbocycle with up to 6 ring atoms.

In a preferred embodiment, one of $R^{17}$ and $R^{18}$ is H and the other is Me.

Further preferred are compounds wherein one of $R^{17}$ and $R^{18}$ is H and the other is phenyl.

In a further preferred embodiment, $R^{17}$ and $R^{18}$ may form a carbocycle with up to 6 ring atoms, wherein n is 0 or 1, all of the above residues being optionally substituted independently of each other.

Physiological substrates of QC in mammals are, e.g. Aβ3-40/42, [Gln$^3$]Aβ3-40/42, [Gln$^3$]Aβ11-40/42, [Gln$^{11}$]Aβ11-40/42, [Gln$^1$]Gastrins (17 and 34), [Gln$^1$]Neurotensin, [Gln$^1$]FPP, [Gln$^1$]TRH, [Gln$^1$]GnRH, [Gln$^1$]CCL 2, [Gln$^1$]CCL 7, [Gln$^1$]CCL 8, [Gln$^1$]CCL 16, [Gln$^1$]CCL 18, [Gln$^1$]ELA, [Gln$^1$]Fractalkine, [Gln$^1$]Orexin A, [Gln$^3$]-glucagon(3-29) and [Gln$^5$]-substance P(5-11). For further details see table 2, The compounds and/or combinations according to the present invention and pharmaceutical compositions comprising at least one inhibitor of QC are useful for the treatment of conditions that can be treated by modulation of QC/EC activity.

TABLE 2

Amino acid sequences of physiological active peptides with an N-terminal glutamine residue

| Peptide | Amino acid sequence | Function |
| --- | --- | --- |
| Gastrin 17 Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH Swiss-Prot: P20396 | QHP amide | TRH functions as a regulator of the biosynthesis of TSH in the anterior pituitary gland and as a neurotransmitter/neuromodulator in the centraL and peripheral nervous systems. |
| GnRH Swiss-Prot: P01148 | QHWSYGL RP(G) amide | Stimulates the secretion of gonadotropins; it stimulates the secretion of both luteinizing and follicle-stimulating hormones. |

TABLE 2-continued

Amino acid sequences of physiological active peptides with an N-terminal glutamine residue

| Peptide | Amino acid sequence | Function |
| --- | --- | --- |
| CCL16 (small inducible cytokine A16) Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neufrophus. Also shows potent myelosuppressive activity, suppresses proliferation of myeloidprogenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8) Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind hepatin. |
| CCL2 (small inducible cytokine A2) Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducibie cytokine A18) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium. binds to cx3crl. |
| CCL7 (small inducible cytokine A7) | QPVGINT STTCCYRFIN KK IPKQRLES YRRTTSSHCP REAVIFKTKL DKEICADPTQ | Chemotactic factor that attracts monocytes and eosinophils, but not neutrophils. Augments |

TABLE 2-continued

Amino acid sequences of physiological active peptides with an N-terminal glutamine residue

| Peptide | Amino acid sequence | Function |
|---|---|---|
| Swiss-Prot: P80098 | KWVQDFMKHL DKKTQTPKL | monocyte anti-tumor activity. Also induces the release of gelatinase B. This protein can bind heparin. Binds to CCR1, CCR2 and CCR3. |
| Orexin A (Hypocretin 1) Swiss-Prot O43612 | QPLPDCCRQK TCSCRLYELL HGAGNHAAGILTL | Neuropeptide that plays a significant role in the regulation of food intake and sleep-wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 *J Physiol* 15 315-324).

The peptide hormone gastrin, released from antral G cells, is known to stimulate the synthesis and release, of histamine from ECL cells in the oxynitic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract, it has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 *Regal Pept* 9337-44).

Neurotensin (NT) is a neuropeptide implicated in the pathophysiology of schizophrenia that specifically modulates neurotransmitter systems previously demonstrated to be misregulated in this disorder Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 *Biol Psychiatry* 50 856-872).

Fertilization promoting peptide (FPP), a tripeptide related to thyrotrophs releasing hormone (TRH), is found In seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being Important, in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 *Vitam dorm* 63, 1-28).

CCL2, CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, humoral and cell-mediated immunity responses, leukocyte adhesion and migration processes at the endothelium.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class 1 major histocompatibility complex. Consequently, in order to conserve full activity of ELA, the formation of PyrELA must be avoided (Beck A. et al, 2001, *J Pept Res* 57(6);528-38).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

To date, inhibition of human QC was only detected initially for 1,10-phenanthroline and reduced 6-methylpterin (Busby, W. H. J. et al 1987 *J Biol Chem* 262, 8532-8536). By a comparison of numerous heterocyclic compounds, the present invention demonstrates that imidazole derivatives inhibit the animal QC. Using the continuous assay (for details see example 1), many imidazole derivatives were analyzed concerning their ability to inhibit the human QC as a member of the highly conserved mammalian QCs.

Thus, the present invention provides imidazole and its derivatives and histidine and its derivatives as activity reducing effectors of QC and their characteristics in terms of inhibition type and potency Structures and Revalues are shown in tables 2 and 3. The results are described in detail in example 2.

TABLE 2

Inhibitory constants of imidazole derivatives in the human QC catalyzed reaction. Determinations were performed at 30° C. in 0.05 M Tris-HCl pH 8.0, containing 5 mM EDTA.

| Compound | $K_I$-value (mM) | Structure |
|---|---|---|
| core structures | | |
| imidazole | 0.103 ± 0.004 | |
| benzimidazole | 0.138 ± 0.005 | |
| N-1 derivatives | | |
| 1-benzylimidazole | 0.0071 ± 0.0003 | |
| 1-methylimidazole | 0.030 ± 0.001 | |
| 1-vinylimidazole | 0.049 ± 0.002 | |
| oxalic acid diimidazolidide | 0.078 ± 0.002 | |
| N-acetylimidazole | 0.107 ± 0.003 | |
| N(trimethylsilyl)-imidazole | 0.167 ± 0.007 | |
| N-benzoylimidazole | 0.174 ± 0.007 | |
| 1-(2-oxo-2-phenyl-ethyl)-imidazole | 0.184 ± 0.005 | |
| 1-(3-aminopropyl)-imidazole | 0.41 ± 0.01 | |
| 1-phenylimidazole | no inhibition | |
| 1,1'-sulfonyldiimidazole | no inhibition | |
| C-4(5) derivatives | | |
| N-omega-acetylhistamine | 0.017 ± 0.001 | |
| L-histidinamide | 0.56 ± 0.04 | |
| H-His-Trp-OH | 0.60 ± 0.03 | |
| U-histidinol | 1.53 ± 0.12 | |
| L-histidine | 4.4 ± 0.2 | |
| 4-imidazole-carboxaldehyde | 7.6 ± 0.7 | |
| imidazole-4-carbonic acid methylester | 14.5 ± 0.6 | |
| L-histamine | 0.85 ± 0.04 | |
| C-4,5 derivatives | | |
| 5-hydroxymethyl-4-methyl-imidazole | 0.129 ± 0.005 | |
| 4-amino-imidazole-5-carbonic acid amide | 15.5 ± 0.5 | |

TABLE 2-continued

Inhibitory constants of imidazole derivatives in the human QC catalyzed reaction. Determinations were performed at 30° C. in 0.05 M Tris-HCl pH 8.0, containing 5 mM EDTA.

| Compound | $K_I$-value (mM) | Structure |
| --- | --- | --- |
| 4,5-diphenyl-imidazole | no inhibition | |
| 4,5-dicyanoimidazole | no inhibition | |
| C-2 derivatives | | |
| 2-methyl-benzylimidazole | 0.165 ± 0.004 | |
| 2-ethyl-4-methyl-imidazole | 0.58 ± 0.04 | |
| 2-aminobenzimidazole | 1.8 ± 0.1 | |
| 2-chloro-1H-benzimidazole | no inhibition | |
| Others | | |
| 3-(1H-imidazol-1-yl)-1-(3-methylbenzo[b]thiophene-2-ylpropan-1-one | 0.0025 ± 0.0001 | 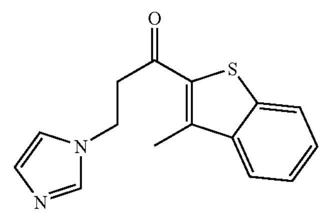 |
| 4-[(1-methyl-1H-imidazol-5-yl)methyl]-3-propyldihydrofuran-2-(3H)-one | 0.0067 ± 0.0003 | 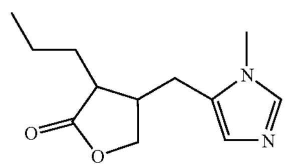 |
| 4-[2-(1H-imidazol-1-yl)-ethoxy]benzoic acid | 0.0034 ± 0.0001 | 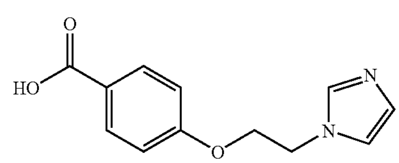 |
| 3-[3-(1H-imidazol-1-yl)propyl]-2-thioxoimidazolidin-4-one | 0.00041 ± 0.00001 | 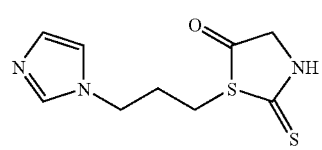 |
| 5-nitro-2-[2-([{3-(1H-imidazol-1-yl-)propyl}amino]carbonyl)phenyl]furamide | 0.0066 ± 0.0004 | 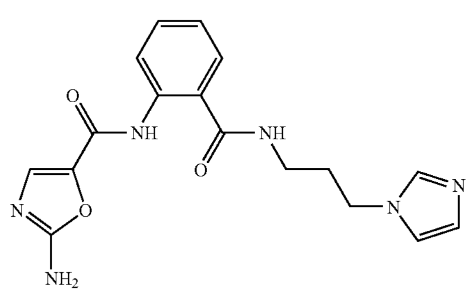 |
| N-(4-chlorophenyl)-N'-[2-(1H-imidazol-1-yl)ethyl]thiourea | 0.00165 ± 0.0007 | 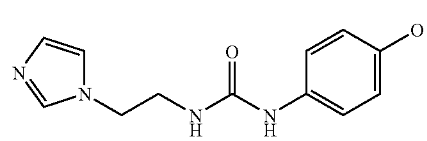 |

TABLE 2-continued

Inhibitory constants of imidazole derivatives in the human QC catalyzed reaction. Determinations were performed at 30° C. in 0.05 M Tris-HCl pH 8.0, containing 5 mM EDTA.

| Compound | $K_I$-value (mM) | Structure |
|---|---|---|
| 2-[(5-imidazol-1-ylmethyl-pyrrolidine-2-carbonyl)-amino]-propionic acid methyl ester | 0.0322 ± 0.0007 | 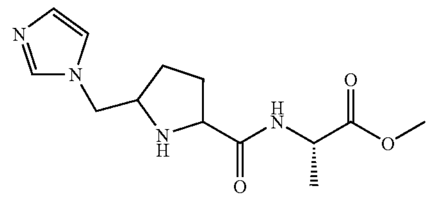 |
| 2-[(5-Imidazol-1-ylmethyl-2,3-dihydro-1H-pyrrole-2-carbonyl)-amino]-propionic acid methyl ester | n.d. | 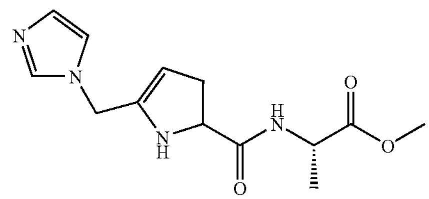 |
| Imidazo[1.5a]pyridine | 0.0356 ± 0.0005 | 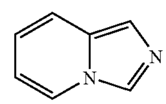 |
| Methyl (2S)-2-{[2S)-2-amino-5-(1H-imidazol-1-ylamino)-5-oxopentanoyl]amino}-3-methylbutanoate | 0.164 ± 0.004 | 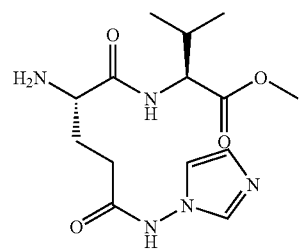 |

TABLE 3

QC inhibition by L-histamine and its two biological metabolites (also known as tele-methylhistamine).

| Compound | $K_I$ value (mM) | Structure |
|---|---|---|
| L-histamine | 0.85 ± 0.04 | 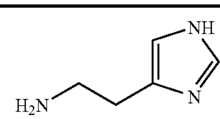 |
| 3-methyl-4-(β-aminoethyl)-imidazole | 0.120 ± 0.004 | 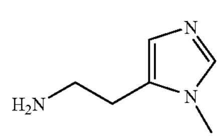 |
| 1-methyl-4-(β-aminoethyl)-imidazole | n.i. | 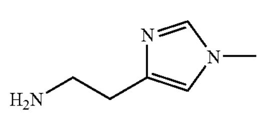 |

Surprisingly, during the characterization of the enzymatic activity it was shown in the present invention that, besides a N-terminal glutaminyl residue, also N-terminal β-homo-glutaminyl residues fulfill properties as substrate of QCs from plants and mammals. The N-terminal β-homo-glutaminyl residue was converted into a five-membered lactam ring by catalysis of human and papaya QC, respectively.

Another preferred embodiment of the present invention comprises screening methods for inhibitors of QC.

A preferred screening method for identifying QC inhibitors from a group of compounds comprises the steps of:
 a) Contacting said compounds with QC under conditions which would permit binding therebetween;
 b) Adding a substrate of QC;
 c) Monitoring the conversion of the substrate or optionally measuring the residual QC activity; and
 d) Calculating changes in the substrate conversion and/or enzyme activity of QC to identify an activity modifying effector.

Another preferred screening method relates to a method for the identification and selection of inhibitors which interact directly or indirectly with the active-site bound metal ion of QC and comprises the following steps:
 a) Contacting said compounds with QC under conditions which would permit binding therebetween;
 b) Adding a substrate of QC which is subject to conversion by QC;
 c) Monitoring the conversion of the substrate or optionally measuring the residual QC activity; and
 d) Calculating changes in the substrate conversion and/or enzyme activity of QC wherein changes may be used to identify an activity modifying effector of QC.

Preferred for the use in the above described screening methods are mammalian QC or *Papaya* QC. Especially preferred is mammalian QC, since the inhibitors identified by these screening methods shall be used for the treatment of diseases in mammals, especially in humans.

By administering a QC-inhibitor and/or a combination according to the present invention to a mammal it can be possible to prevent or alleviate or treat conditions selected from Alzheimer's disease, Down Syndrome, ulcer disease and gastric cancer with or w/o *Helicobacter pylori* infections, neoplasia, inflammatory host responses, cancer, melanoma, malign metastasis, psoriasis, rheumatoid arthritis, atherosclerosis, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Furthermore, by administration of a QC-inhibitor and/or a combination according to the present invention to a mammal it can be possible to stimulate the proliferation of myeloid progenitor cells.

In addition, the administration of a QC-inhibitor and/or a combination according to the present invention can lead to suppression of male fertility.

In a preferred embodiment, the present invention provides the use of inhibitors of QC/EC activity in combination with inhibitors of DP IV or DP IV-like enzymes for the treatment or alleviation of conditions that can be treated by modulation of QC and/or DP IV activity.

In a preferred embodiment, the present invention provides the use of inhibitors of QC/EC activity in combination with inhibitors of PEP for the treatment or alleviation of conditions that can be treated by modulation of QC/EC and/or PEP activity.

Further preferred for the treatment of neuronal diseases is the use of at least one QC-inhibitor in combination with NPY-receptor-ligands, NPY agonists and/or NPY antagonists.

Further preferred for the treatment of neuronal diseases is the use of at least one QC-inhibitor in combination with at least one acetylcholinesterase (ACE) inhibitor.

The present invention provides pharmaceutical compositions for parenteral, enteral or oral administration, comprising at least one inhibitor of QC (EC) optionally in combination with customary carriers and/or excipients; or comprising at least one inhibitor of QC (EC) in combination with at least one PEP-inhibitor and/or at least one DP IV-inhibitor and/or at least one NPY-reeeptor-ligand, optionally in combination with customary carriers and/or excipients.

These combinations provide a particularly beneficial effect on behavioral conditions and such combinations are therefore shown to be effective and useful for the treatment of neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

Accordingly, the invention provides a method for the treatment of neuronal disorders (Alzheimer's disease, Down Syndrome, Parkinson disease, Corea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysingulation, anorexia, anxiety related disorders including depression, seizures including epilepsy, drag withdrawal and alcoholism, neurodegenerative disorders including cognitive dysfunction and dementia).

The method comprises either co-administration of a QC-inhibitor and/or at least one PEP-inhibitor and/or at least one DP IV-inhibitor and/or at least one NPY-receptor-ligand and/or at least one ACE-inhibitor or the sequential administration thereof.

Co-administration includes administration of a foundation which includes at least one QC-inhibitor and/or at least one PEP-inhibitor and/or at least one DP IV-inhibitor and/or at least one NPY-receptor-ligand and/or at least one ACE-inhibitor or the essentially simultaneous administration of separate formulations of each agent.

In another aspect the invention provides the use of at least one QC-inhibitor and/or at least one PEP-inhibitor and/or at least one DP IV-inhibitor and/or at least one NPY-receptor-ligand and/or at least one ACE-inhibitor for use in the manufacture of a composition for the treatment of neuronal disorders.

The present invention provides pharmaceutical compositions for parenteral, enteral or oral administration, comprising at least one inhibitor of QC (EC) optionally in combination with customary carriers and/or excipients; or comprising at least one inhibitor of QC in combination with at least one DP IV-inhibitor, optionally in combination with customary carriers and/or excipients.

Suitable inhibitors of prolyl endopeptidase are, e.g. chemical derivatives of proline or small peptides containing terminal prolines. Benzyloxycarbonyl-prolyl-prolinal has been shown to be a specific transition state inhibitor of the enzyme (Wilk, S. and Orloeski, M., J. Neurochem., 41, 69 (1983), Friedman, et al., Neurochem, 42, 237 (1984)). N-terminal substitutions of L-proline or L-prolylpyrrolidine (Atack, et al., Eur. J. of Pharm., 205, 157-163 (1991), JP 03 56,460, EP 384,341), as well as variations of N-benzyloxycarbonyl (Z) dipeptides containing prolinal at the carboxy terminus have been synthesized as prolyl endopeptidase inhibitors (Nishikata, et al., Chem. Pharm. Bull. 34(7), 2931-2936 (1986), Baker, A. et al., Bioorganic & Medicinal Chem. Letts., 1(11), 585-590 (1991)). Thioproline, thiazolidine, and oxopyrrolidine substitutions of the core structure have been reported to inhibit prolyl endopeptidase (Tsuru, et al., J. Biochem., 94, 1179 (1988), Tsuru, et al., J. Biochem., 104, 580-586 (1988), Saito et al., J. Enz. Inhib. 5, 51-75 (1991), Uchida, I., et al. PCT Int. Appl. WO 90 12,005, JP 03 56,461, JP 03 56,462). Similarly, various modifications of the carboxy terminal proline have been made, including various fluorinated ketone derivatives (Henning, EP 4,912,127). General syntheses of fluorinated ketone derivatives has been described (Angelastro, M. R., et al, Tetrahedron Letters 33(23), 3265-3268 (1992)). Other compounds such as chloromethyl ketone derivatives of acyl-proline or acylpeptide-proline (Z-Gly-Pro-$CH_2CL$) have been demonstrated to inhibit the enzyme by alkylating the enzyme's active site (Yoshimoto, T., et al., Biochemistry 16, 2942 (1977)), EP-A-0 286 928 discloses 2-acylpyrrolidine derivatives useful as propyl endopeptidase inhibitors.

Further suitable prolyl endopeptidase inhibitors according to the present invention are, e.g. Fmoc-Ala-Pyrr-CN and those listed below:

Z-321
Zeria Pharmaceutical Co Ltd

ONO-1603
Ono Pharmaceutical Co Ltd

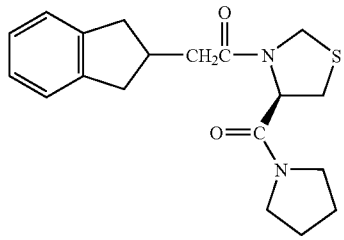

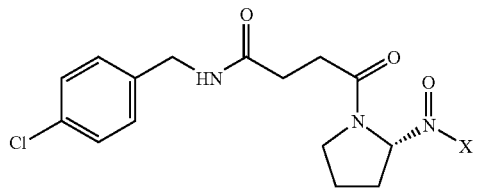

(4R)-3-(indan-2-ylacetyl)-4-
(1-pyrrolidinyl-carbonyl)-
1,3-thiazolidin
JTP-4819
Japan Tobacco Inc (S)-1-[N-(4-chlorobenzyl)-
succinamoyl]pyrrolidin-2-
carbaldehyd
S-17092
Servier

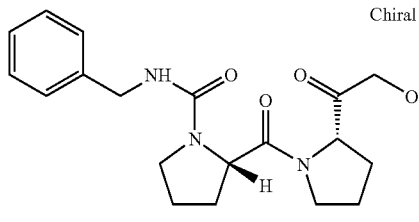

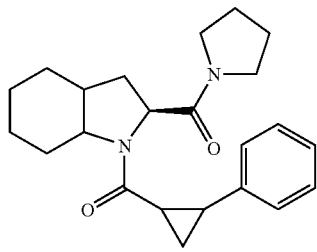

(S)-2-{[(S)•(hydroxyacatyl)-1-
pyrrolidinyl]carbonyl}-N-
(phenylmethyl)-1-pyrrolidin-
carboxamid (2S, 3sS, 7aS)-1{[(R,R)-2-
phenylcyclopropyl]
carbonyl] octahydro-1H-
indol Further suitable prolyl endopeptidase inhibitors according to the present invention are disclosed in JP 01042465, JP 03031298, JP 04208299, WO 0071144, U.S. Pat. No. 5,847,155; JP 09040693, JP 10077300, JP 05331072, JP 05015314, WO 9515310, WO 9300361, EP 0556482, JP 06234693, JP 01068396, EP 0709373, U.S. Pat. Nos. 5,965,556, 5,756,763, 6,121,311, JP 63264454, JP 64000069, JP 63162672, EP 0268390, EP 0277588, EP 0275482, U.S. Pat. Nos. 4,977,180, 5,091,406, 4,983,624, 5,112,847, 5,100,904, 5,254,550, 5,262,431, 5,340,832, 4,956,380, EP 0303434, JP 03056486, JP 01143897, JP 1226880, EP 0280956, U.S. Pat. No. 4,857,537, EP 0461677, EP 0345428, 4JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. Nos. 5,073,549, 4,999,349, EP 0268281, U.S. Pat. No. 4,743,616, BP 0232849, EP 0224272, JP 62114978, JP 62114957, U.S. Pat. Nos. 4,757,083, 4,810,721, 5,198,458, 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 9118877, JP 04009367, JP 04235162, US 5407950, WO 9501352, JP 01250370, JP 02207070, U.S. Pat. No. 5,221,752, EP 0468339, JP 04211648 and WO 9946272, the teachings of which are herein incorporated by reference in their entirety, especially concerning these inhibitors, their definition, uses and their production.

Suitable DP IV-inhibitors are are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, boronyl inhibitors and cyclopropyl-fused pyrrolidines. Inhibitors of dipeptidyl peptidase IV are described in U.S. Pat. Nos. 6,011,155; 6,107,317; 6,110,949; 6,124,305; 6,172,081; WO 99/61431, WO 99/67278, WO 99/67279, DE 198 34 591, WO 97/40832, DE 196 16 486 C 2, WO 95/15309, WO 98/19998, WO 00/07617, WO 99/38501, WO 99/46272, WO 99/38501, WO 01/68603, WO 01/40180, WO 01/81337, WO 01/81304, WO 01/55105, WO 02/02560, WO 01/34594, WO 02/38541 (Japanese), WO 02/083128, WO 03/072556, WO 03/002593, WO 03/000250, WO 03/000180, WO 03/000181, EP 1 258 476, WO 03/002553, WO 03/002531, WO 03/002530, WO 03/004496, WO 03/004498, WO 03/024942, WO 03/024965, WO 03/033524, WO 03/035057, WO 03/035067, WO 03/037327, WO 03/040174, WO 03/045977, WO 03/055881, WO 03/057144, WO 03/057666, WO 03/068748, WO 03/068757, WO 03/082817, WO 03/101449, WO 03/101958, WO 03/104229, WO 03/74500, WO 04/007446, WO 04/007468, WO 04/018467, WO 04/018468, WO 04/018469, WO 04/026822, the teachings of which are herein incorporated by reference in their entirety concerning the inhibitors, their production and their use.

Preferred DP IV-inhibitors include valine pyrrolidide (Novo Nordisk), NVP-DPP728A (1-[[[2-[{5-cyanopyridin-2-yl}amino]ethyl]amino]acetyl]-2-cyano-(S)-pyrrolidine) (Novartis) as disclosed by Hughes et al., Biochemistry, 38 (36), 11597-11603, 1999, LAF-237 (1-[(3-hydroxyadamant-1-ylamino)-acetyl]-pyrrolidine-2(S)-carbonitrile); disclosed by Hughes et al., Meeting of the American Diabetes Association 2002, Abstract no. 272 or (Novartis), TSL-225(tryptophyl-1,2,3,4-tetrahydroisoquinoline-3-carboxylic acid), disclosed by Yamada et. al., Bioorg. & Med. Chem. Lett. 8 (1998), 1537-1540, 2-cyanopyrrolidides and 4-cyanopyrrolidides as disclosed by Asworth et al, Bioorg. & Med. Chem. Lett., 6, No. 22, pp 1163-1166 and 2745-2748 (1996), EE-999011 ([(2S)-1-([2'S]-2'-amino-3,3'dimethyl-butanoyl)-pyrrolidine-2-carbonitrile]), disclosed by Sudre et al., Diabetes 51 (5), pp 1461-1469 (2002) (Ferring), GW-229A (GlaxoSmithKline), disclosed by Kandhawa S A, et at, ACS Meeting 2003, 226th:New York (MEDI 91), 815541 (Tanabe/GlaxoSmithKline), MK-431 (Merck & Co), PT-100 (Point Therapeutics) and the compounds disclosed in WO 01/34594 (Guilford), employing dosages as set out in the above references. For the avoidance of doubt, the examples disclosed in each of the above mentioned publications are specifically incorporated herein by reference in their entirety, as individually disclosed compounds, especially concerning their structure, their definition, uses and their production.

Other suitable agents that can be used according to the present invention in combination with QC-inhibitors are NPY, a NPY mimetic or a NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988, the disclosures in all of which documents are hereby incorporated by reference. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)-N2-(diphenylacetyl)-(R)-N-[1-(4-hydroxy-phenyl)ethyl] arginine amide (Example 4 of international patent application WO 99/15498).

For the avoidance of doubt the examples disclosed in each of the above mentioned publications are specifically incorporated herein by reference in their entirety, as individually disclosed compounds, especially concerning their structure, their definition, uses and their production.

Preferred DP IV-inhibitors are dipeptide-like compounds and compounds analogous to dipeptide compounds that are formed from an amino acid and a thiazolidine or pyrrolidine group, and salts thereof, referred to hereinafter as dipeptide-like compounds. Preferably the amino acid and the thiazolidine or pyrrolidine group are bonded with an amide bond. Such compounds are disclosed in WO 99/61431.

Especially suitable for that purpose according to the invention are dipeptide-like compounds in which the amino acid is preferably selected from a natural amino acid, such as, for example, leucine, valine, glutamine, glutamic acid, proline, isoleucine, asparagines and aspartic acid.

The dipeptide-like compounds used according to the invention exhibit at a concentration (of dipeptide compounds) of 10 μM, a reduction in the activity of plasma dipeptidyl peptidase IV or DP IV-analogous enzyme activities of at least 10%, especially of at least 40%. Frequently a reduction in activity of at least 60% or at. least 70% is also required. Preferred agents may also exhibit a reduction in activity of a maximum of 20% or 30%.

Preferred compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine of formulas 8 and 9:

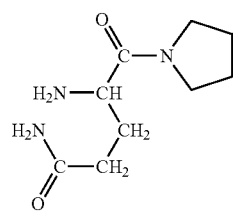

(8)

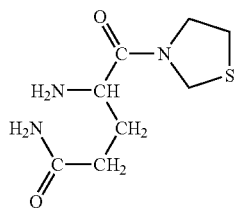

(9)

Further preferred compounds are given in Table 4.

The salts of the dipeptide-like compounds can be present in a molar ratio of dipeptide (-analogous) component to salt component of 1:1 or 2:1. Such a salt is, for example, (Ile-Thia)$_2$ fumaric acid.

TABLE 4

Structures of further preferred dipeptide compounds
DP IV inhibitor

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine Further preferred DP IV-inhibitors are (1) Peptide structures as disclosed in WO 03/002593. e.g. t-butyl-Gly-Pro-D-Val, t-butyl-Gly-Pro-Gly, t-butyl-Gly-Pro-Ile, t-butyl-Gly-Pro-Ile-amide, t-butyl-Gly-Pro-t-butyl-Gly, t-butyl-Gly-Pro-Val, (2) Peptidylketones as disclosed in WO03/033524, e.g. 2-Methylcarbonyl-1-N-[(L)-Alanyl-(L)-Valinyl]-(2S)-pyrrolidine hydrobromide; 2-Methyl)carbonyl-1-N-[(L)-Valinyl-(L)-Prolyl-(L)-Valinyl]-(2S)-pyrrolidine hydrobromide; 2-[(Acetyl-oxy-methyl)carbonyl]-1-N-[(L)-Alanyl-(L)-Valinyl]-(2S)-pyrrolidine hydrobromide; 2-[Benzoyl-oxymethyl)carbonyl]-1-N-[{(L)-Alanyl}-(L)-Valinyl]-(2S)-pyrrolidine hydrobromide; 2-{[(2,6-Dichlorbenzyl)thiomethyl]carbonyl}-1-N-[{(L)-Alanyl}-(L)-Valinyl]-(2S)-pyrrolidine; 2-[Benzoyloxy-methyl)carbonyl]-1-N-[Glycyl-(L)-Valinyl]-(2S)-pyrrolidine hydrobromide; 2-[([1,3]-thiazole-2-yl)carbonyl]-1-N-[{(L)-Alanyl}-(L)-Valinyl]-(2S)-pyrrolidine trifluoracetat; 2-[(benzothiazole-2-yl)carbonyl]-1-N-[N-{(L)-Alanyl}-(L)-Valinyl]-(2S)-pyrrolidin trifluoracetat; 2-[(-benzothiazole-2-yl)carbonyl]-1-N-[{(L)-Alanyl}-Glycyl]-(2S)-pyrrolidine trifluoracetat; 2-[(pyridin-2-yl)carbonyl]-1-N-[N-{(L)-Alanyl}-(L)-Valinyl]-(2S)-pyrrolidine trifluoracetat.

(3) Substituted aminoketone compounds as disclosed in WO 03/040174, e.g. 1-cyclopentyl -3-methyl-1-oxo-2-pentanaminium chloride, /-cyclopentyl-3-methyl -1-oxo-2-butanaminium chloride, 1-cyclopentyl-3,3-dimethyl-1-oxo-2-butanaminium chloride, 1-cyclohexyl-3,3-dimethyl-1-oxo-2-butanaminium chloride, 3-(cyclopentylcarbonyl) -1,2,3,4-tetrahydroisoquinolinium chloride, and N-(2-cyclopentyl-2-oxoethyl)cyclohexanaminium chloride.

(4) Side-chain modified DP IV-inhibitors as disclosed in WO 01/14318, and (5) Prodrugs of DP IV-inhibitors, as disclosed in WO 99/67278 and WO 99/67279.

For the avoidance of doubt, the examples disclosed in each of the above mentioned publications under (1) to (5) are specifically incorporated herein by reference in their entirety, as individually disclosed compounds, especially concerning their structure, their definition, uses and their production.

Pharmaceutical Compositions

To prepare the pharmaceutical compositions of this invention, at least one effector of QC optionally in combination with at least one PEP-inhibitor and/or at least one DP IV-inhibitor and/or at least one NPY-receptor-ligand and/or at least one ACE-inhibitor, can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gel caps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the Salter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carbosymethylcellulose, methylcellulose, polyvinylpyrrolidone or gelatin.

Where the processes for the preparation of the compounds of the present invention give rise to mixture of stereoisomers, these isomers may be separated by conventional techniques such as preparative chromatography. The compounds may be prepared in racemic form, or individual enantiomers may he prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may he achieved by means of conventional protecting groups, such as those described in *Protective Groups in Organic Chemistry*, ed. J. F. W. McOmie, Plenum Press, 1973; and T. W. Greene & P. G. M Wuts, *Protective Groups in Organic Synthesis*, John Wiley & Sons, 1991. The protecting groups may be removed at a convenient subsequent stage using conventional methods known from the art.

The method of treating neuronal disorders as described in the present invention, may also he carried out using a pharmaceutical composition at least one effector of QC optionally in combination with at least one PEP-inhibitor and/or at least one DP IV-inhibitor and/or at least one NPY-receptor-ligand and/or at least one ACE-inhibitor or any other of the compounds as defined herein and a pharmaceutically acceptable carrier. The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention maybe administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art To be administered in the form of transdermal delivery system, the dosage administration will, of course, be continuous rather than intermittent throughout the dosage regimen. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polydroxyethylaspartamide-ephenol, or polyethyl eneoxide-polyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels. Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 trig/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

Suitably, the particularly beneficial effect provided by the treatment of the invention is an Improved therapeutic ratio for the combination of the invention relative to the therapeutic ratio for one compound of the combination when used alone and at a dose providing an equivalent efficacy to the combination of the invention.

In a preferred aspect, the particularly beneficial effect provided by the treatment of the invention is indicated to be a synergistic effect relative to the control expected from the effects of the individual active agents.

In a further aspect of the invention, combining doses of at least one QC-inhibitor with at least one PEP-inhibitor and/or at least one DP IV-inhibitor and/or at least one NPY-receptor-ligand will produce a greater beneficial effect than can be achieved for either agent alone at a dose twice that used for that agent in the combination.

In a preferred aspect, the dosage level of each of the active agents when used in accordance with the treatment of the invention will he less than would have been required from a purely additive effect upon the neuronal condition.

It is also considered that the treatment of the invention will effect an improvement, relative to the individual agents, in decreasing the intracellular deposition of pGlu-amyloid-□-peptides and thereby dramatically slowing down the plaque formation in the brain of a mammal, preferably In human brain.

In a further aspect, the invention also provides a process for preparing a pharmaceutical composition comprising at least one at least one effector of QC optionally in combination with at least one PEP-inhibitor and/or at least one DP IV-inhibitor and/or at least one NPY-receptor-ligand and/or at least one ACE-inhibitor and a pharmaceutically acceptable carrier therefor, which process comprises admixing the QC effector and/or DP IV-inhibitor and/or the PEP-inhibitor and/or the NPY-receptor-ligand and/or the ACE-inhibitor and a pharmaceutically acceptable carrier.

The compositions are preferably in a unit dosage form in an amount appropriate for the relevant daily dosage.

Suitable dosages, including especially unit dosages, of the QC-inhibitor, the PEP-inhibitor, the DP IV-inhibitor and the NPY-receptor-ligand include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES OF THE INVENTION

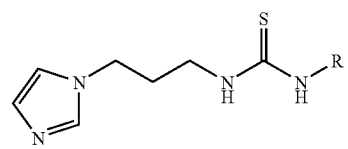

| Example | R | ESI-MS (M + H) | Ki (µM) |
|---|---|---|---|
| 1 | $CH_3$ | 199.29 | 13 |
| 2 | $CH(CH_3)$ | 241.37 | 14.7 |
| 3 | $CH_2C_6H_5$ | 275.39 | 5.67 |
| 4 | $C_6H_5$ | 261.36 | 4.4 |
| 5 | P F-phenyl | 279.35 | 4.73 |
| 6 | P Cl-phenyl | 295.80 | 1.2 |
| 7 | P ethyl-phenyl | 289.41 | 2.78 |
| 8 | P (triflourmethyl)-phenyl | 329.4 | 3.93 |
| 9 | (p methoxy-carbonyl)-phenyl | 319.4 | 1.19 |
| 10 | P (methyl-carbonyl)-phenyl | 303.40 | 1.79 |
| 11 | P (methoxy)-phenyl | 291.40 | 0.70 |

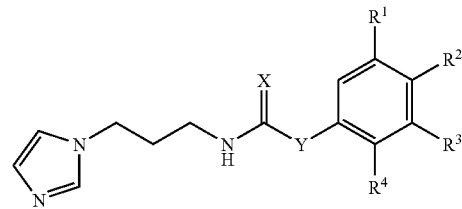

| Example | $R^1$ | $R^2$ | $R^3$ | $R^4$ | X | Y | ESI-MS (M + H) | Ki (µM) |
|---|---|---|---|---|---|---|---|---|
| 12 | H | OMe | H | H | S | NH | 291.4 | 0.700 |
| 13 | OMe | H | H | H | S | NH | 291.40 | 1.86 |
| 14 | H | OMe | H | OMe | S | NH | 321.41 | 0.565 |
| 15 | OMe | H | OMe | H | S | NH | 321.41 | 0.751 |
| 16 | H | OMe | OMe | H | S | NH | 321.41 | 0.088 |
| 17 | OMe | OMe | OMe | H | S | NH | 351.40 | 0.34 |
| 18 | H | O—$CH_2$—O | | H | S | NH | 305.4 | 5.66 |
| 19 | H | O—$CH_2$—$CH_2$—O | | H | S | NH | 319.4 | 1.12 |
| 20 | H | OEt | H | H | S | NH | 305.4 | 0.89 |
| 21 | H | SMe | H | H | S | NH | 307.5 | 1.66 |
| 22 | H | OMe | OMe | H | O | NH | 305.4 | 0.461 |
| 23 | H | OMe | OMe | H | S | $CH_2$ | 320.4 | 0.387 |

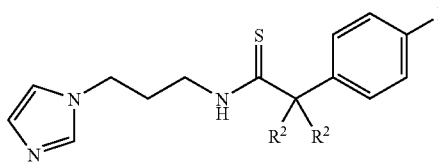
| Example | R1 | R1 | R1 | ESI-MS (M + H) | Ki (μM) |
|---|---|---|---|---|---|
| 24 | H | H | H | 260.3 | |
| 25 | H | Me | H | 274.4 | |
| 26 | H | H | Me | 274.4 | |
| 27 | OMe | —(CH$_2$)$_2$— | | 316.4 | 2.22 |
| 28 | Cl | —(CH$_2$)$_3$— | | 334.9 | |
| 29 | Cl | —(CH$_2$)$_4$— | | 348.9 | |
| 30 | OMe | —(CH$_2$)$_5$— | | 358.5 | 0.425 |
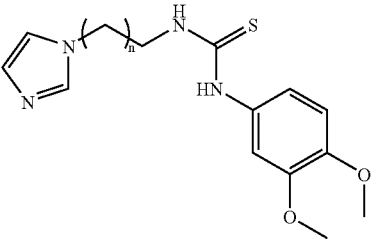
| Example | N | ESI-MS (M + H) | Ki (μM) |
|---|---|---|---|
| 36 | 1 | 307.4 | 17.66 |
| 37 | 3 | 335.4 | 0.55 |
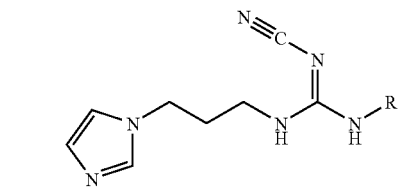
| Example | R | ESI-MS (M + H) | Ki (μM) |
|---|---|---|---|
| 31 | Me | 207.30 | 1.5 |
| 32 | p methyl-phenyl | 283.3 | 1.34 |
| 33 | phenyl | 269.3 | 1.02 |
| 34 | p-methyl-phenyl | 299.3 | 0.71 |
| 35 | 3,4-dimethoxyphenyl | 329.4 | 1.36 |
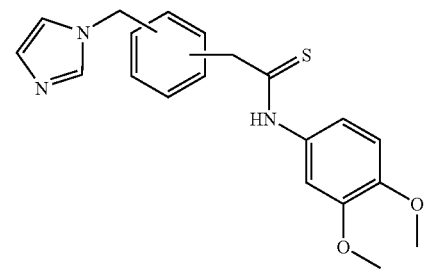
| Example | position | ESI-MS (M + H) | Ki (μM) |
|---|---|---|---|
| 38 | para | 383.5 | 1.86 |
| 39 | ortho | 383.5 | |
| 40 | meta | 383.5 | 3.52 |
Synthesis of the Examples
Synthesis scheme 1: synthesis of the examples 1-22, 36, 37
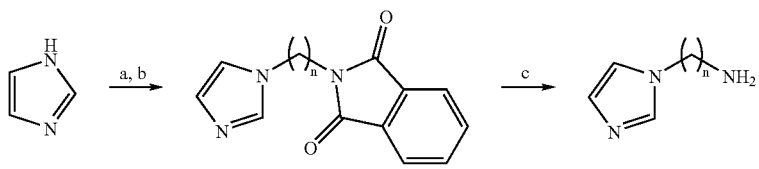

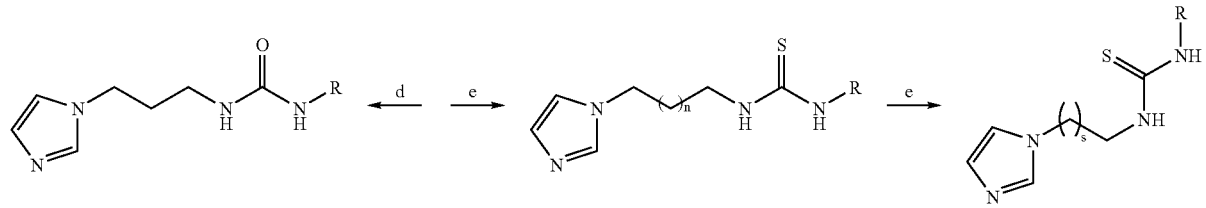

Reagents and conditions: (a) NaH, DMF, 4h, rt; (b) ?-?, 8h, 100° C.; (c) H₂N—NH₂, EtOH, 8h, reflux then 4N HCl, 6h, reflux, (d) R—NCO, EtOH, 6h, reflux, (e) R—NCS, 6h, reflux Synthesis scheme 2: synthesis of the examples 23-30

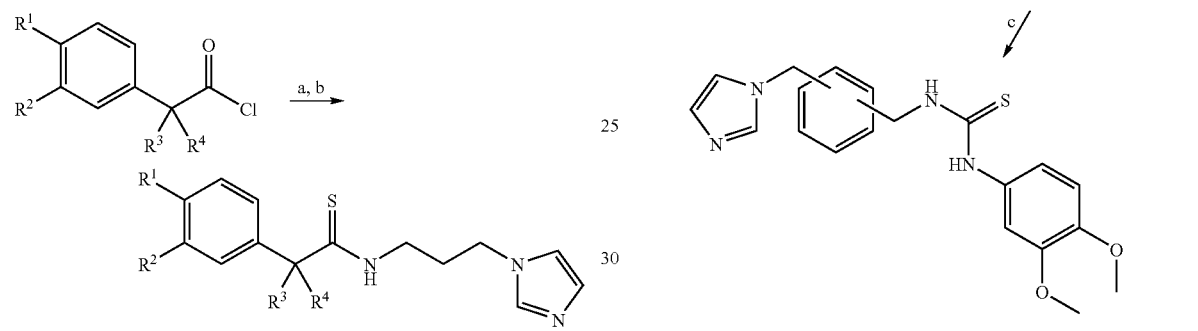

Reagents and conditions: (a) 1H-imidazole-1-propanamine, CH₂Cl₂, rt., 1h; (b) Laweson's Reaent, EtOH, reflux. 8h Synthesis scheme 3: synthesis of the examples 31-35

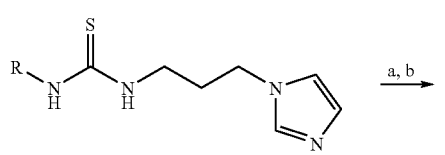

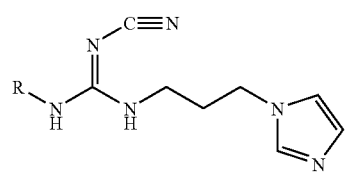

Reagents and conditions: (a) MeI, CH₂Cl₂, rt., 1h; (b) H₂N—CN, BuOH, reflux, 8h

Synthesis scheme 4: synthesis of the examples 38-40

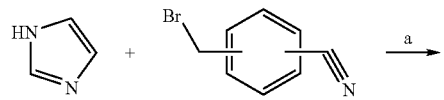

-continued

Reagents and conditions: (a) NaH, DMF, rt., 3h; (b) LiAlH₄, dioxane, reflux, 1h; (e) R—NCS, EtOH, reflux 6h, Example 1-21

1H-imidazole-1-propanamine was reacted with the corresponding isothiocyanate in ethanol under reflux for 8h. After that the solvent was removed and the remaining oil was desolved in methylene chloride. The organic layer was washed twice with a saturated solution of NaHCO₃ followed by NaHSO₄ and brine, dried then evaporated. The remaining solid was recrystallised from ethyl acetate, yielding the example thiourea in yields of 80-98%.

Example 22

1H-imidazole-1-propanamine was reacted with the corresponding 2,3-dimethoxy-isocyanate in ethanol under reflux for 8h. After that the solvent was removed and the remaining oil was desolved in methylene chloride. The organic layer was washed twice with a saturated solution of NaHCO₃ followed by NaHSO₄ and brine, dried then evaporated. The remaining solid was recrystallised from ethyl acetate, giving 22 with yields of 85%.

Example 23-30

1H-imidazole-1-propanamine was reacted with the corresponding 2-phenyl acetyl chloride in methylene chloride adding one equivalent of tri ethyl amine. After 2h the solvent was removed and the remaining oil was dissolved in dioxane adding Laweson's Reagent. After stirring for 1.5 h a saturated solution of NaHCO₃ was added. Dioxane was evaporated and the aqueous layer was extrcated by means of ethyl acetate.

The organic layer was separated, dried and the solvent was evaporated. The remaining solid was crystallized from acetyl acetate/ether, giving 23-30 with total yields of 62-85%.

Example 31-35

All examples were made from the corresponding thioureas by reacting with MeI yielding the thiouronium salts. These intermediates were dissolved in butanole and cyanamide was added. After heating under reflux for 8 h butanole was removed and to the remaining oil 0.1M HCl was added. The aqueous layer was extracted by means of methylene chloride. After phase separation the aqueous layer was brought to pH10 and again extracted by means of methylene chloride. Then the organic layer was dried and evaporated giving 31-35 with yields from 40-87%.

Example 36, 37

The 17H-imidazole-1-alkylamines were prepared according to the literature from □-brom-alkylphtalimides and imidazoiium salt and subsequent hydrazinolysis. The resulting products were transformed into the thioureas according to example 1-21 giving a 88% (example 36) and 95% (example 37) yield.

Example 38-40

Imidazole was reacted with the corresponding brommethylphenylcyanide in DMF, utilizing 1 equivalent of NaH for 3 h under rt, giving the 1H-imidazole-1-methylphenylcyamides. The solvent was removed and the resulting oil was redissolved in dioxane. The cyanides were converted in the corresponding amines using 1 equivalent of $LiAlH_4$. After adding a saturated solution of $KHSO_4$, dioxane was evaporated and the aqueous layer was extracted by means of $CHCl_3$. The organic layer was concentrated in vacuo and the amine was converted in the corresponding thioureas according to example 1-21 giving a 78% (example 38) and 65% (example 39) and 81% (example 39) yield.

Solid Phase Synthesis of Peptides

The peptides used herein were synthesized with an automated synthesizer SYMPHONY (RAININ) using a modified Fmoc-protocol. Cycles were modified by using double couplings from the 15$^{th}$ amino acid from the C-terminus of the peptide with five-fold excess of Fmoc-amino acids and coupling reagent. The peptide couplings were performed by TBTU/NMM-activation using a 0.23 mmol substituted NovaSyn TGR-resin or the corresponding preloaded Wang-resin at 25 μmol scale. The cleavage from the resin was carried out by a cleavage-cocktail consisting of 94.5% TFA, 2.5% wafer, 2.5% EDT and 1% TIS.

Analytical and preparative HPLC were performed by using different gradients on the LiChrograph HPLC system of Merck-Hitachi. The gradients were made up from two solvents: (A) 0.1% TFA in $H_2O$ and (B) 0.1% TFA in acetonitrile. Analytical HPLC were performed under the following conditions: solvents were run (1 ml/min) through a 125-4 Nucleosil RP18-column, over a gradient, from 5%-50% B over 15 min and then up to 95% B until 20 min, with UV detection λ=220 nm). Purification of the peptides was carried out by preparative HPLC on either a 250-20 Nucleosil 100 RP8-column or a 250-10 LiChrospher 300 RP18-column (flow rate 6 ml/min, 220 nm) under various conditions depending on peptide chain length.

For the identification of the peptides and peptide analogues, laser desorption mass spectrometry was employed using the HP G2025 MALDI-TOF system of Hewlett-Packard.

Biological Evaluation

Example 1

Determination $IC_{50}$-Values of DP IV-Inhibitors

100 μl inhibitor stock; solution were mixed with 100 μl buffer (HEPES pH 7.6) and 50 μl substrate (Gly-Pro-pNA, final concentration 0.4 mM) and preincubated at 30° C. Reaction was started by addition of 20 μl purified porcine DP IV. Formation of the product pNA was measured at 405 nm over 10 min using the HTS 7000Plus plate reader (Perkin Elmer) and slopes were calculated. The final inhibitor concentrations ranged between 1 mM and 30 nM. For calculation of $IC_{50}$-values GraFit 4.0.13 (Erithacus Software) was used.

Example 2

Determination of $K_i$-Value of DP IV-Inhibitors

For determination of the $K_i$-values DP IV activity was measured in the same way as described in example 2 at final substrate concentrations of 0.05, 0.1, 0.2, and 0.4 mM and further 7 inhibitor concentrations covering the $IC_{50}$ concentration. Calculations were performed using the GraFit Software.

Example 3

Prolyl Endopeptidase (PEP) Enzymatic Activity Assays

The enzymatic activity of PEP was quantified as described recently (Schulz et al., 2002, Modulation of inositol 1,4,5-triphosphate concentration by prolyl endopeptidase inhibition. Eur J Biochem 269: 5813-5820). Cellular extracts as described above were incubated in the assay buffer using the fluorogenic substrate Z-Gly-Pro-NHMec (10 μM; Bachem, Heidelberg, Germany) on a spectrofluorimeter SFM 25 (excitation wavelength 380 nm, emission wavelength 460 nm, Kontron, Neufahm, Germany) equipped with a four-cell changer and controlled by an IBM-compatible personal computer. The data obtained were analyzed with the software FLUCOL (Machleidt et al, 1995).

Example 4

Assays for Glutaminyl Cyclase Activity

Fluorometric Assays

All measurements were performed with a BioAssay Reader HTS-7000Plus for microplates (Perkin Elmer) at 30° C. QC activity was evaluated fluorometrically using H-Gln-, βNA. The samples consisted of 0.2 mM fluorogenic substrate, 0.25 U pyroglutamyl aminopeptidase (Unizyme, Horsholm, Denmark) in 0.2 M Tris/HCl, pH 8.0 containing 20 mM EDTA and an appropriately diluted aliquot of QC in a final volume of 250 μl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 μmol pGlu-βNA from H-Gln-pNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 μl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 *J Neurosci Methods* 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 μL Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 5

Characterization of Effectors of QC

Imidazole Derivatives

Imidazole and benzimidazole derivatives carrying substituents in different positions of the 5-membered ring were tested as inhibitors of QC (Table 3). The constitution of the numbers refers to the imidazole ring. The applied methods are described in example 1.

C-4(5) and C-4,5 derivatives. The compounds carrying substitutions in either in the constitutionally equivalent 4- or 5-position of the imidazole ring or in both positions showed a diminished potency for inhibition of human QC. The only exception, however, comprised N-ω-acetylated histamine that proved to be one of the most potent inhibitory compounds. Small substituents in these positions had only little effect on binding as indicated by the similar inhibition constant of 5-hydroxymethyl-4-methyl-imidazole compared to imidazole. Larger and more bulky groups attached to these sites diminished or abolished binding of the compound by the enzyme. Some of the other substituents tested are known to exert negative inductive or mesomeric effects that are capable to reduce the electron density in the imidazole ring, which also contributes to poorer binding constants. The difference in the $K_i$-values of L-histidine and histidinamide also indicate some influence of the charge on binding. Evidence for electrostatic repulsion of charged substrates were already shown in the substrate specificity studies, i.e. glutaminamide was readily converted to products by human QC, but no reactivity was observed for free glutamine as substrate.

C-2 derivatives. Ail derivatives tested inhibited QC more weakly as imidazole. Any substitution bigger than a proton hinders proper QC-binding. Only due to the methyl group in 2-methyl-benzimidazole, the inhibition constant drops about one order of magnitude. A very similar relation was shown by comparison of the $K_i$-values for benzimidazole and 2-amino-benzimidazole. Additionally, the results indicate that the influence is not related to electronic alterations.

N-1 derivatives. Among the imidazole derivatives tested on inhibition of human QC, most compounds that had improved $K_i$-values compared to imidazole showed alterations at one nitrogen atom. These compounds also contained one of the most effective QC inhibitors, 1-benzylimidazole. Interestingly, only little alterations of this structure led to a loss of inhibitory quality, as can be seen for 1-benzoylimidazole and phenylimidazole, which was inactive under the experimental conditions. Also in this case, the observed changes seemed not to be only caused by a reduced electron density of the imidazole ring due to the negative mesomeric effect of the Phenyl group, because also the bulky trimethyl-silyl group, exhibiting a positive inductive effect showed reduced binding compared to other residues. Interestingly, one of the less effective compounds of this group was 1-aminopropyl-imidazole. The small efficacy of this compound is caused by the basic amino group, since the sterically similar compounds 1-methylimidazole and 1-vinylimidazole showed improved binding to the active site. Thus, the positively charged amino group accounts for the smaller $K_i$-values, a result that is corroborated by a comparison of the $K_i$-values of N-to-acetylated histamine (Table 3) and histamin (Table 4).

Effect of 3,4 and 3,5 derivatization. The imidazole derivatives that contained substituents in positions 4(5) or both were shown to have a restricted efficiency for binding to the enzyme. The effect of the specific substitutions were specified by comparison of the inhibitory constants of L-histamine and the two intermediates in the biological degradation of histamine, 3-methyl-4-histamine and 3-methyl-5-histamine (Table 4). L-Histamine revealed a $K_i$ value that was about one order of magnitude smaller compared to its acetylated counterpart. Methylation of one nitrogen resulted in a considerable improvement of efficacy in case of 3-methyl-4-histamine. Methylation leading to 3-methyl-5-histamine, however, resulted in a complete loss of inhibitory activity. Thus, the observed effect seems to be mainly caused by a sierical hindrance of binding due to the derivatisation of the carbon adjacent to the basic nitrogen. Presumably, the basic nitrogen plays a key role for binding to the enzyme.

Example 6

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 µl) were mixed with equal volumes of the matrix solution. For matrix solution we used DHAP/DAHC, prepared by solving 30 mg 2',6'-dihydroxyacetophenone (Aldrich) and 44 mg diammonium hydrogen citrate (Fluka) in 1 ml acetonitrile/ 0.1% TFA in water (1/1, v/v). A small volume (≈1 µl) of the matrix-analyte-mixture was transferred to a probe tip and immediately evaporated In a vacuum chamber (Hewlett-Packard G2024A sample prep accessory) to ensure rapid and homogeneous sample crystallization.

For long-term testing of Glu$^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ3(3-21) a] concentrations, and 0.2 U QC was added all 24 hours, in case of Aβ(3-21)a, the assays contained 1% DMSO. At different times, samples were removed from the assay tube, peptides extracted using ZipTips (Millipore) according to the manufacturer's recommendations., mixed with matrix solution (1:1v/v) and subsequently the mass spectra recorded. Negative controls did either contain no QC or heat deactivated enzyme. For the inhibitor studies the sample composition was the same as described above, with exception of the inhibitory compound added (5 mM benzimidazole or 2 mM 1,10-phenanthroline).

What is claimed is:

1. A method of treatment of Alzheimer's disease comprising administering to a mammal in need thereof a therapeutically effective amount of a compound of formula 2a or a pharmaceuticaly acceptable salt or stereoisomer thereof:

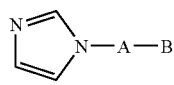

formula 2a wherein:
A is selected from the group consisting of:

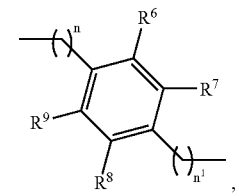

(I)

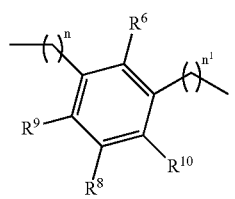

(II)

and

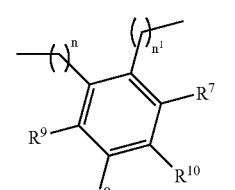

(III)

wherein
R$^6$-R$^{10}$ are H or methyl;
n and n$^1$ are 1;
and
B is

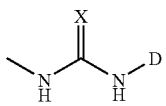

wherein:
D represents substituted phenyl, wherein the substitutent is -oxyalkyl, -thioalkyl, or halogenyl; or D represents dihydrobenzodioxine, benzodioxole, benzodithiole dihydrobenzodithiine, benzooxathiole or dihydorbenzooxathiine; and
X represents O, S, or N—CN.

2. A method of treatment of Alzheimer's disease comprising administering to a mammal in need thereof a therapeutically effective amount of a pharmaceutical composition for parenteral, enteral or oral administration, comprising at least one compound of formula 2a or a pharmaceuticaly acceptable salt or stereoisomer thereof, optionally in combination with a therapeutically acceptable carrier or excipient:

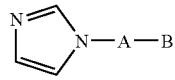

formula 2a wherein:
A is selected from the group consisting of:

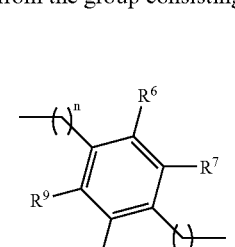

(I)

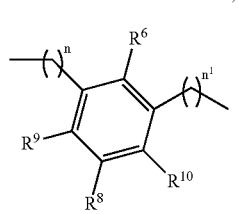

(II)

and

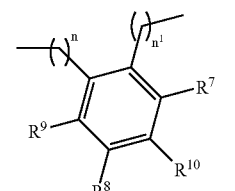

(III)

wherein
R$^6$-R$^{10}$ are H or methyl;
n and n$^1$ are 1;
and
B is

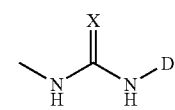

wherein:
D represents substituted phenyl, wherein the substitutent is -oxyalkyl, -thioalkyl, or halogenyl; or D represents dihydrobenzodioxine, benzodioxole, benzodithiole dihydrobenzodithiine, benzooxathiole or dihydorbenzooxathiine; and
X represents O, S, or N—CN.

3. A method of treatment of Alzheimer's disease comprising administering to a mammal in a need thereof a therapeutically effective amount of a pharmaceutical composition comprising (i) at least one compound of formula 2a or a pharmaceutically acceptable salt or stereoisomer thereof and (ii) at least one agent selected from the group consisting of PEP-inhibitors, inhibitors of DP IV/DP IV-like enzymes, NPY-receptor ligands, NPY antagonists and ACE inhibitors; optionally in combination with a therapeutically acceptable carrier or excipient:

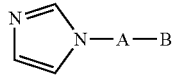

formula 2a wherein:
A is selected from the group consisting of:

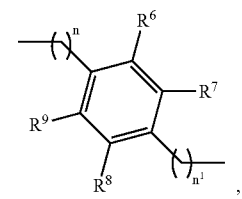
(I)

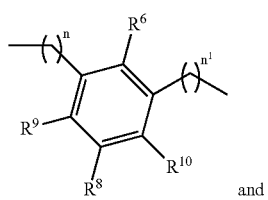
(II)

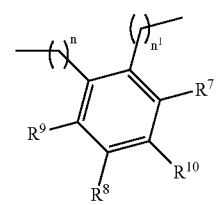
(III)

wherein
$R^6$-$R^{10}$ are H or methyl;
n and $n^1$ are 1;
and
B is

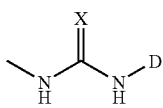

wherein:
D represents substituted phenyl, wherein the substitutent is -oxyalkyl, -thioalkyl, or halogenyl; or D represents dihydrobenzodioxine, benzodioxole, benzodithiole dihydrobenzodithiine, benzooxathiole or dihydorbenzooxathiine; and
X represents O, S, or N—CN.

4. The method according to claim 1, wherein $R^6$-$R^{10}$ are H.
5. The method according to claim 1, wherein X is S.
6. The method according to claim 4, wherein X is S.
7. The method according to claim 1, wherein D is 3,4-(dimethoxy)-phenyl.
8. The method according to claim 4, wherein D is 3,4-(dimethoxy)-phenyl.
9. The method according to claim 5, wherein D is 3,4-(dimethoxy)-phenyl.
10. The method according to claim 6, wherein D is 3,4-(dimethoxy)-phenyl.
11. The method according to claim 1, wherein the compound of formula 2a is selected from the group consisting of:

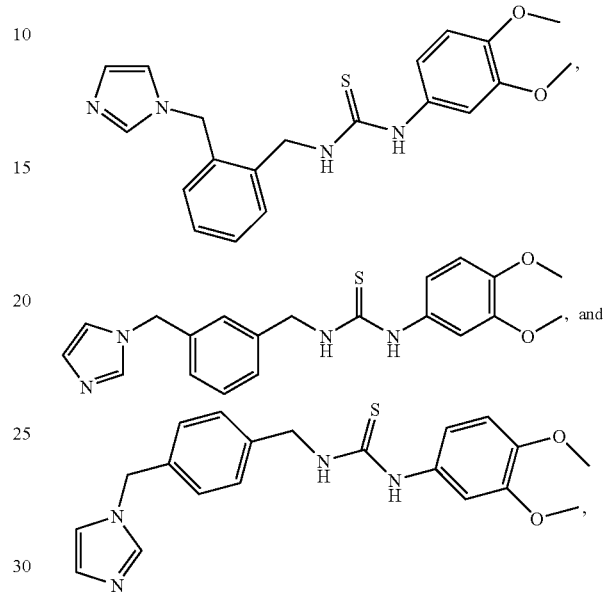

or a pharmaceuticaly acceptable salt or stereoisomer thereof.

12. The method according to claim 3, wherein said inhibitor of DP IV/DP IV-like enzymes is selected from the group consisting of L-threo-isoleucyl pyrrolidide, L-allo-isoleucyl thiazolidide, L-allo-isoleucyl pyrrolidide; and salts thereof or valine pyrrolidide, NVP-DPP728A (1-[[[2-[{5-cyanopyridin-2-yl}amino]ethyl]amino]acetyl]-2-cyano-(S)-pyrro-lidine) LAF-237 (1-[(3-hydroxy-adamant-1-ylamino)-acetyl]-pyrrolidine -2(S)-carbonitrile); TSL-225 (tryptophyl-1,2,3,4-tetrahydroisoquinoline-3-carboxylic acid), FE-999011 ([(2S)-1-([2'S]-2'-amino-3',3'dimethyl-butanoyl)-pyrrolidine-2-carbonitrile]), GW-229A, 815541, MK-431 and PT-100 (Point Therapeutics).

13. The method according to claim 3, wherein said NPY antagonist is selected from the group consisting of 3a,4,5,9b-tetrahydro-1h-benz[e]indol-2-yl amine, BIBP3226 and (R)-N2-(diphenylacetyl)-(R)-N-[1-(4-hydroxy-phenyl)ethyl] arginine amide.

14. The method according to claim 3, wherein said PEP-inhibitor is selected from the group consisting of chemical derivatives of proline or small peptides containing terminal prolines, e.g. benzyloxycarbonyl-prolyl-prolinal, N-terminal substituted L-proline or L-prolylpyrrolidine, substituted N-benzyloxycarbonyl (Z) dipeptides containing prolinal at the carboxy terminus, substituted thioprolines, substituted thiazolidines, substituted oxopyrrolidines, carboxy terminal modified prolines including fluorinated ketone derivatives, chloromethyl ketone derivatives of acyl-proline or acylpeptide-proline (Z-Gly-Pro-CH$_2$Cl) and 2-acylpyrrolidine derivatives.

15. The method according to claim 3, wherein said PEP-inhibitor is selected from the group consisting of Fmoc-Ala-Pyrr-CN, Z-321, ONO-1603, JTP-4819 and S-17092.

16. The method according to claim 3, wherein said ACE-inhibitor is SDZ ENA 713 (rivastigmine (+)-(S)-N-ethyl-3-[(1-dimethylamino)ethyl]-N-methylphenylcarbamate hydrogen tartrate).

17. The method according to claim 1, wherein X represents S or N—CN.

18. The method according to claim 3, wherein X represents S or N—CN.

* * * * *

SEQUENCE LISTING

```
<160> NUMBER OF SEQ ID NOS: 25

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40
```

```
<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 5

Asp Ala Glu Phe Arg His Asp Ser Gly Tyr Glu
1               5                   10

<210> SEQ ID NO 6
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (9)..(9)
<223> OTHER INFORMATION: AMIDATION

<400> SEQUENCE: 6

Glu Phe Arg His Asp Ser Gly Tyr Glu
1               5

<210> SEQ ID NO 7
<211> LENGTH: 21
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (21)..(21)
<223> OTHER INFORMATION: AMIDATION

<400> SEQUENCE: 7

Asp Ala Glu Phe Arg His Asp Ser Gly Tyr Glu Val His His Gln Lys
1               5                   10                  15

Leu Val Phe Phe Ala
            20

<210> SEQ ID NO 8
<211> LENGTH: 19
<212> TYPE: PRT
<213> ORGANISM: Artificial sequence
<220> FEATURE:
<223> OTHER INFORMATION: synthetic peptide
<220> FEATURE:
```

```
<221> NAME/KEY: MOD_RES
<222> LOCATION: (19)..(19)
<223> OTHER INFORMATION: AMIDATION

<400> SEQUENCE: 8

Glu Phe Arg His Asp Ser Gly Tyr Glu Val His His Gln Lys Leu Val
1               5                   10                  15

Phe Phe Ala

<210> SEQ ID NO 9
<211> LENGTH: 38
<212> TYPE: PRT
<213> ORGANISM: Artificial sequence
<220> FEATURE:
<223> OTHER INFORMATION: Synthetic peptide

<400> SEQUENCE: 9

Gln Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 10
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (19)..(19)
<223> OTHER INFORMATION: AMIDATION

<400> SEQUENCE: 10

Gln Phe Arg His Asp Ser Gly Tyr Glu Val His His Gln Lys Leu Val
1               5                   10                  15

Phe Phe Ala

<210> SEQ ID NO 11
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: AMIDATION

<400> SEQUENCE: 11

Asp Ala Gln Phe Arg His Asp Ser Gly Tyr Glu
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 12
```

```
-continued

Gln Phe Arg His Asp Ser Gly Tyr Glu
1               5

<210> SEQ ID NO 13
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 13

Gln Gly Pro Trp Leu Glu Glu Glu Glu Ala Tyr Gly Trp Met Asp
1               5                   10                  15

Phe

<210> SEQ ID NO 14
<211> LENGTH: 13
<212> TYPE: PRT
<213> ORGANISM: Homo sapiens

<400> SEQUENCE: 14

Gln Leu Tyr Glu Asn Lys Pro Arg Arg Pro Tyr Ile Leu
1               5                   10

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 15

Gln His Trp Ser Tyr Gly Leu Arg Pro Gly
1               5                   10

<210> SEQ ID NO 16
<211> LENGTH: 97
<212> TYPE: PRT
<213> ORGANISM: Homo sapiens

<400> SEQUENCE: 16

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
            35                  40                  45

Asn Arg Glu Val Cys Thr Asn Pro Asn Asp Asp Trp Val Gln Glu Tyr
        50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                85                  90                  95

Gln

<210> SEQ ID NO 17
<211> LENGTH: 76
<212> TYPE: PRT
```

<213> ORGANISM: Homo sapiens

<400> SEQUENCE: 17

```
Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

<210> SEQ ID NO 18
<211> LENGTH: 76
<212> TYPE: PRT
<213> ORGANISM: Homo sapiens

<400> SEQUENCE: 18

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

<210> SEQ ID NO 19
<211> LENGTH: 68
<212> TYPE: PRT
<213> ORGANISM: Homo sapiens

<400> SEQUENCE: 19

```
Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
            20                  25                  30

Cys Pro Lys Pro Gly Val Ile Leu Leu Thr Lys Arg Gly Arg Gln Ile
        35                  40                  45

Cys Ala Asp Pro Asn Lys Lys Trp Val Gln Lys Tyr Ile Ser Asp Leu
    50                  55                  60

Lys Leu Asn Ala
65
```

<210> SEQ ID NO 20
<211> LENGTH: 373
<212> TYPE: PRT
<213> ORGANISM: Homo sapiens

<400> SEQUENCE: 20

```
Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30
```

-continued

Ser Cys Gly Lys Arg Ala Ile Ile Leu Glu Thr Arg Gln His Arg Leu
          35                  40                  45

Phe Cys Ala Asp Pro Lys Glu Gln Trp Val Lys Asp Ala Met Gln His
 50                  55                  60

Leu Asp Arg Gln Ala Ala Ala Leu Thr Arg Asn Gly Gly Thr Phe Glu
 65                  70                  75                  80

Lys Gln Ile Gly Glu Val Lys Pro Arg Thr Thr Pro Ala Ala Gly Gly
                  85                  90                  95

Met Asp Glu Ser Val Val Leu Glu Pro Glu Ala Thr Gly Glu Ser Ser
              100                 105                 110

Ser Leu Glu Pro Thr Pro Ser Gln Glu Ala Gln Arg Ala Leu Gly
              115                 120                 125

Thr Ser Pro Glu Leu Pro Thr Gly Val Thr Gly Ser Ser Gly Thr Arg
          130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                  165                 170                 175

Ala Pro His Gln Pro Gly Pro Ser Leu Trp Ala Glu Ala Lys Thr Ser
              180                 185                 190

Glu Ala Pro Ser Thr Gln Asp Pro Ser Thr Gln Ala Ser Thr Ala Ser
          195                 200                 205

Ser Pro Ala Pro Glu Glu Asn Ala Pro Ser Glu Gly Gln Arg Val Trp
210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                  245                 250                 255

Gly Ser Met Ala His Val Ser Val Pro Val Ser Ser Glu Gly Thr
              260                 265                 270

Pro Ser Arg Glu Pro Val Ala Ser Gly Ser Trp Thr Pro Lys Ala Glu
          275                 280                 285

Glu Pro Ile His Ala Thr Met Asp Pro Gln Arg Leu Gly Val Leu Ile
                  290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                  325                 330                 335

Thr Tyr Gln Ser Leu Gln Gly Cys Pro Arg Lys Met Ala Gly Glu Met
              340                 345                 350

Ala Glu Gly Leu Arg Tyr Ile Pro Arg Ser Cys Gly Ser Asn Ser Tyr
          355                 360                 365

Val Leu Val Pro Val
    370

<210> SEQ ID NO 21
<211> LENGTH: 76
<212> TYPE: PRT
<213> ORGANISM: Homo sapiens

<400> SEQUENCE: 21

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
              20                  25                  30

```
Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
 50                  55                  60

Lys His Leu Asp Lys Lys Thr Gln Thr Pro Lys Leu
 65                  70                  75
```

<210> SEQ ID NO 22
<211> LENGTH: 33
<212> TYPE: PRT
<213> ORGANISM: Homo sapiens

<400> SEQUENCE: 22

```
Gln Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
                20                  25                  30

Leu
```

<210> SEQ ID NO 23
<211> LENGTH: 11
<212> TYPE: PRT
<213> ORGANISM: Homo sapiens

<400> SEQUENCE: 23

```
Arg Pro Lys Pro Gln Gln Phe Phe Gly Leu Met
 1               5                  10
```

<210> SEQ ID NO 24
<211> LENGTH: 7
<212> TYPE: PRT
<213> ORGANISM: Artificial sequence
<220> FEATURE:
<223> OTHER INFORMATION: Synthetic peptide

<400> SEQUENCE: 24

```
Gln Gln Phe Phe Gly Leu Met
 1               5
```

<210> SEQ ID NO 25
<211> LENGTH: 27
<212> TYPE: PRT
<213> ORGANISM: Artificial sequence
<220> FEATURE:
<223> OTHER INFORMATION: Synthetic peptide

<400> SEQUENCE: 25

```
Gln Gly Thr Phe Thr Ser Asp Tyr Ser Lys Tyr Leu Asp Ser Arg Arg
 1               5                  10                  15

Ala Gln Asp Phe Val Gln Trp Leu Met Asn Thr
                20                  25
```